United States Patent
Dakshanamurthy et al.

(10) Patent No.: US 10,806,725 B2
(45) Date of Patent: *Oct. 20, 2020

(54) SMALL MOLECULE INHIBITORS OF XBP1 SPLICING

(71) Applicant: GEORGETOWN UNIVERSITY, Washington, DC (US)

(72) Inventors: Sivanesan Dakshanamurthy, Herndon, VA (US); Milton L. Brown, Brookeville, MD (US); Robert Clarke, Rockville, MD (US); Ayesha N. Shajahan-Haq, Haymarket, VA (US); Jacqueline Smith, Bowie, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,258

(22) Filed: May 16, 2016

(65) Prior Publication Data
US 2017/0007588 A1   Jan. 12, 2017

Related U.S. Application Data

(63) Continuation of application No. 14/009,969, filed as application No. PCT/US2012/032110 on Apr. 4, 2012, now Pat. No. 9,359,299.
(Continued)

(51) Int. Cl.
| | | |
|---|---|---|
| *A61K 31/4439* | (2006.01) | |
| *A61K 31/426* | (2006.01) | |
| *A61K 31/427* | (2006.01) | |
| *C07D 401/04* | (2006.01) | |
| *C07D 401/14* | (2006.01) | |

(Continued)

(52) U.S. Cl.
CPC .......... *A61K 31/4439* (2013.01); *A61K 31/41* (2013.01); *A61K 31/426* (2013.01); *A61K 31/427* (2013.01); *A61K 31/444* (2013.01); *A61K 45/06* (2013.01); *C07D 213/32* (2013.01); *C07D 401/04* (2013.01); *C07D 401/14* (2013.01); *C07D 405/14* (2013.01); *C07D 417/04* (2013.01); *C07D 417/14* (2013.01)

(58) Field of Classification Search
None
See application file for complete search history.

(56) References Cited

U.S. PATENT DOCUMENTS

| | | |
|---|---|---|
| 7,858,666 B2 | 12/2010 | Patterson et al. |
| 2004/0157861 A1 | 8/2004 | Scarborough et al. |

(Continued)

FOREIGN PATENT DOCUMENTS

| | | |
|---|---|---|
| WO | 2007101224 | 9/2007 |
| WO | 2008036308 | 3/2008 |
| WO | 2009091815 | 7/2009 |

OTHER PUBLICATIONS

Database accession No. 1001834-54-3, Database Registry Chemical Abstracts Service, Feb. 6, 2008.
(Continued)

*Primary Examiner* — Savitha M Rao
*Assistant Examiner* — Andrew P Lee
(74) *Attorney, Agent, or Firm* — Kilpatrick Townsend & Stockton LLP

(57) ABSTRACT

Small molecule inhibitors of XBP1 splicing by IRE1α are provided, as well as methods for their use in treating or preventing cancer (e.g., endocrine resistant breast cancer), diabetes, and obesity.

16 Claims, 5 Drawing Sheets

Related U.S. Application Data

(60) Provisional application No. 61/471,479, filed on Apr. 4, 2011.

(51) Int. Cl.

| | | |
|---|---|---|
| *C07D 405/14* | (2006.01) | |
| *C07D 417/04* | (2006.01) | |
| *C07D 417/14* | (2006.01) | |
| *A61K 31/41* | (2006.01) | |
| *C07D 213/32* | (2006.01) | |
| *A61K 31/444* | (2006.01) | |
| *A61K 45/06* | (2006.01) | |

(56) References Cited

U.S. PATENT DOCUMENTS

| | | |
|---|---|---|
| 2005/0288347 A1 | 12/2005 | Hodge et al. |
| 2010/0196357 A1 | 8/2010 | Huang et al. |
| 2011/0065162 A1 | 3/2011 | Patterson et al. |
| 2011/0070297 A1 | 3/2011 | Cao et al. |

OTHER PUBLICATIONS

Database accession No. 1002567-56-7, Database Registry Chemical Abstracts Service, Feb. 11, 2008.
Database accession No. 1011042-58-2, Database Registry Chemical Abstracts Service, Mar. 31, 2008.
Database accession No. 1012685-25-4, Database Registry Chemical Abstracts Service, Apr. 7, 2008.
Database accession No. 1090469-80-9, Database Registry Chemical Abstracts Service, Dec. 26, 2008.
Database accession No. 1181152-13-5, Database Registry Chemical Abstracts Service, Sep. 8, 2009.
Database accession No. 1181912-51-5, Database Registry Chemical Abstracts Service, Sep. 10, 2009.
Database accession No. 1182568-67-7, Database Registry Chemical Abstracts Service, Sep. 11, 2009.
Database accession No. 1211765-73-9, Database Registry Chemical Abstracts Service, Mar. 19, 2010.
Database accession No. 1211810-32-0, Database Registry Chemical Abstracts Service, 2010.
Database accession No. 332157-92-3, Database Registry Chemical Abstracts Service, Apr. 24, 2001.
Database accession No. 332158-99-3, Database Registry Chemical Abstracts Service, 2001.
Database accession No. 521322-40-7, Database Registry Chemical Abstracts Service, May 28, 2003.
Database accession No. 749881-04-7, Database Registry Chemical Abstracts Service, Sep. 23, 2004.
Database accession No. 808186-66-5, Database Registry Chemical Abstracts Service, Jan. 5, 2005.
Database accession No. 852679-77-7, Database Registry Chemical Abstracts Service, Jun. 22, 2005.
Database accession No. 892042-73-8, Database Registry Chemical Abstracts Service, Jul. 11, 2006.
Database accession No. 897784-70-2, Database Registry Chemical Abstracts Service, Aug. 1, 2006.
Database accession No. 919205-53-1, Database Registry Chemical Abstracts Service, Feb. 4, 2007.
Gene Card for IRF-1, http://www.genecards.org/cgi-bin/carddisp.pl?gene=IRF1, 2006.
Proceedings of the 102nd Annual Meeting of the American Association for Cancer Research, Orlando,FL. Philadelphia (PA): AACR; Cancer Research, vol. 71, 8 Suppl):Abstract No. 2070. doi:10.1158/1538-7445.AM2011-2070, Apr. 2011.
Resistance to Anti-Estrogen Therapy in Breast Cancer Due to Natural Cell Response, Georgetown University Medical Center, release date Apr. 4, 2011.
Systemic treatment of early breast cancer by hormonal, cytotoxic, or immune therapy, EBCTCG Early Breast Cancer Trialists' Collaborative Group, Lancet, 339, 1992, pp. 1-15.
Tamoxifen for early breast cancer: an overview of the randomised trials, EBCTCG Early Breast Cancer Trialists, Collaborative Group, Lancet, vol. 351, issue 9114, May 16, 1998, pp. 1451-1467.
U.S. Appl. No. 14/009,969, Final Office Action dated Aug. 27, 2015, 9 pages.
U.S. Appl. No. 14/009,969, Non-Final Office Action dated Jan. 30, 2015, 9 pages.
U.S. Appl. No. 14/009,969, Notice of Allowance dated Feb. 18, 2016, 8 pages.
U.S. Appl. No. 14/009,969, Restriction Requirement dated Jul. 31, 2014, 8 pages.
Bagratuni et al., XBP1s levels are implicated in the biology and outcome of myeloma mediating different clinical outcomes to thalidomide-based treatments, Blood 116(2), Jul. 2010, pp. 250-253.
Berenbaum, Synergy, additivism and antagonism in immunosuppression, Clinical & Experimental Immunology, vol. 28, Apr. 1977, pp. 1-18.
Brünner et al., Effect of growth and cell cycle kinetics of estradiol and tamoxifen on MCF-7 human breast cancer cells grown in vitro in nude mice, Cancer Research, vol. 49, Mar. 15, 1989, pp. 1515-1520.
Brünner et al., MCF7/LCC2: A 4-hydroxytamoxifen resistant human breast cancer variant which retains sensitivity to the steroidal antiestrogen ICI 182, 780, Cancer Research, vol. 53, issue 14, Jul. 15, 1993, pp. 3229-3232.
Clarke et al., Acquired estrogen independence and antiestrogen resistance in breast cancer, Estrogen receptor driven phenotypes, Trends Endocrinol Metab, vol. 7, issue 8, Oct. 1996, pp. 25-35.
Clarke et al., Cellular and molecular pharmacology of antiestrogen action and resistance, Pharmacol Rev, vol. 53, issue 1, Mar. 2001, pp. 25-71.
Clarke et al., Gene network signaling in hormone responsiveness modifies apoptosis and autophagy in breast cancer cells, J Steroid Biochem Mol Biol, vol. 1114, issue 1-2, Mar. 2009, pp. 8-20.
Clarke, Issues in experimental design and endpoint analysis in the study of experimental cytotoxic agents in vivo in breast cancer and other models, Breast Cancer Res Treat, vol. 46, issue 2-3, 1997, pp. 255-278.
Clarke, The effects of a constitutive production of TGF-a on the growth of MCF-7 human breast cancer cells in vitro and in vivo, Mol Endocrinol, vol. 3, Feb. 1989, pp. 372-380.
Clarke et al., The inter-relationships between ovarian-independent growth, antiestrogen resistance and invasiveness in the malignant progression of human breast cancer, J Endocrinol, vol. 122, 1989, pp. 331-340.
Cox et al., Transcriptional induction of genes encoding endoplasmic reticulum resident proteins requires a transmembrane protein kinase, Cell, 73, 1993, pp. 1197-1206.
Danziger et al., Automated site-directed drug design: a general algorithm for knowledge acquisition about hydrogen-bonding regions at protein surfaces, Proceedings of the Royal Society of London. Series B, Biological Sciences, 236(1283), 1989, pp. 101-113.
Davenport et al., Heat shock protein inhibition is associated with activation of the unfolded protein response pathway in myeloma plasma cells, Blood, 110(7), 2007, pp. 2641-2649.
Davenport et al., Untangling the unfolded protein response, Cell Cycle, 7(7), 2008, pp. 865-869.
Davies et al., Expression and Splicing of the Unfolded Protein Response Gene XBP-1 are significantly associated with Clinical Outcome of Endocrine-treated Breast Cancer, International Journal of Cancer, vol. 123, Issue 1, Jul. 2008, pp. 85-88.
Delarosa et al., Tri-substituted triazoles as potent non-nucleoside inhibitors of the HIV-1 reverse transcriptase, Bioorganic & Medicinal Chemistry Letters, vol. 16, No. 17, Sep. 1, 2006, pp. 4444-4449.
Doerrler et al., Regulation of the dolichol pathway in human fibroblasts by the endoplasmic reticulum unfolded protein response, Proc Natl Acad Sci, vol. 96, Nov. 9, 1999, pp. 13050-13055.

(56) References Cited

OTHER PUBLICATIONS

Dowsett et al., International Web-based consultation on priorities for translational breast cancer research, Breast Cancer Research, vol. 9, Issue 6, Nov. 2007, p. R81.

Durose et al., Intrinsic capacities of molecular sensors of the unfolded protein response to sense alternate forms of endoplasmic reticulum stress, Mol Biol Cell, vol. 17, issue 7, Jul. 2006, pp. 3095-3107.

European Application No. EP12768320.9, Extended European Search Report dated Sep. 12, 2014, 14 Pages.

*European Application No. EP12768320.9, Office Action dated Apr. 26, 2016, 5 pages.

European Application No. EP12768320.9, Office Action dated Oct. 13, 2015, 5 pages.

Ferretti et al., Second- and third-generation aromatase inhibitors as first-line endocrine therapy in postmenopausal metastatic breast cancer patients: a pooled analysis of the randomized trials, Br J. Cancer, vol. 94, Jun. 19, 2006, pp. 1789-1796.

Foulkes et al., Estrogen receptor status in BRCA1- and BRCA2-related breast cancer: the influence of age, grade and histological type, Clin Cancer Res., 10, 2004, pp. 2029-2034.

Frandsen et al., Assays for the study of human cancer cell invasion and metastasis, Fibrinolysis, vol. 6 (suppl 4), 1992, pp. 71-76.

Gomez et al., Human X-Box binding protein-1 confers both estrogen independence and antiestrogen resistance in breast cancer cell lines, FASEB J, vol. 21, issue 14, Dec. 2007, pp. 4013-4027.

Gorczynski et al., Allosteric inhibition of the protein-protein interaction between the leukemia-associated proteins Runx1 and CBFbeta, Chemistry & Biology, 14, 2007, pp. 1186-1197.

Gorczynski, Synthesis and evaluation of substituted 4-aryloxy- and 4-arylsulfanyl-phenyl-2-aminothiazoles as inhibitors of human breast cancer cell proliferation, Bioorganic & Medicinal Chemistry, 12, 2004, pp. 1029-1036.

Gu et al., Association of interferon regulatory factor-1, nucleophosmin, nuclear factor-kappaB, and cyclic AMP response element binding with acquired resistance to faslodex (ICI 182,780), Cancer Research, vol. 62, Jun. 15, 2002, pp. 3428-3437.

Han et al., IRE1alpha kinase activation modes control alternate endoribonuclease outputs to determine divergent cell fates, Cell, 138(3), 2009, pp. 562-575.

Hanfelt, Statistical approaches to experimental design and data analysis of in vivo studies, Breast Cancer Research and treatment, vol. 46, issue 2-3, Nov. 1997, pp. 279-302.

Hayflick, Subculturing human diploid fibroblasts, In: P. F. Kruze and M. K. Patterson (eds.), Tissue Culture: Methods and Applications, Academic Press: New York, 1973, pp. 220-223.

Hirota et al., Quantitative measurement of spliced XBP1 mRNA as an indicator of endoplasmic reticulum stress, J Toxicol.Science, vol. 31, issue 2, May 2006, pp. 149-156.

Howell et al., Fulvestrant, Formerly ICI 182,780, Is as Effective as Anastrozole in Postmenopausal Women With Advanced Breast Cancer Progressing After Prior Endocrine Treatment, Journal of Clinical Oncology, vol. 20, Issue 16, Aug. 2002, pp. 3396-3403.

Howell et al., Response to a Specific Antioestrogen (ICI 182,780) in Tamoxifen-resistant Breast Cancer, Lancet, vol. 345, 1995, pp. 29-30.

Iwakoshi et al., Plasma cell differentiation and the unfolded protein response intersect at the transcription factor XBP-1, Nat. Immunol., 4(4), 2003, pp. 321-329.

Iwawaki et al., Analysis of the XBP1 splicing mechanism using endoplasmic reticulum stress-indicators, Biochem Biophys Res Commun, vol. 350, issue 3, Nov. 24, 2006, pp. 709-715.

James et al., Constitutive expression of the steroid sulfatase gene supports the growth of MCF-7 human breast cancer cells in vitro and in vivo, Endocrinology, vol. 142, issue 4, Apr. 2001, pp. 1497-1505.

Jemal et al., Cancer Statistics, 2006, CA: A Cancer Journal for Clinicians, vol. 56, 2006, pp. 106-130.

Jemal et al., Cancer Statistics, 2009, A Cancer Journal for Clinicians, vol. 59, issue 4, 2009, pp. 225-249.

Jiang et al., Glucose-Regulated Protein 78 Antagonizes Cisplatin and Adriamycin in Human Melanoma Cells, Carcinogenesis, 2008.

Lee et al., Proteasome inhibitors disrupt the unfolded protein response in myeloma cells, Proc. Natl Acad, Sci, vol. 100, issue 17, Jun. 30, 2003, pp. 9946-9951.

Lee, Statistics for toxicology, In: B. Ballantyne, T. Marrs and P. Turner (eds.), General and Applied Toxicology, Macmillan Press: New York, 1993, pp. 39-48.

Lee et al., Structure of the dual enzyme Ire1 reveals the basis for catalysis and regulation in nonconventional RNA splicing, Cell, vol. 132, issue 1, Jan. 11, 2008, pp. 89-100.

Leonessa et al., Effect of tamoxifen on the multidrug-resistant phenotype in human breast cancer cells: isobologram, drug accumulation and gp-170 binding studies, Cancer Research, vol. 54, issue 2, Jan. 15, 1994, pp. 441-447.

Leonessa et al., The biology of breast tumor progression: acquisition of hormone-independence and resistance to cytotoxic drugs, Acta Oncol, vol. 31, 1991, pp. 115-123.

Mantel, Evaluation of survival data and two new rank order statistics arising in its consideration, Cancer Chemother Rep, vol. 50, issue 3, 1966, pp. 163-170.

Ogata et al., Autophagy is Activated for Cell Survival After Endoplasmic Reticulum Stress, Molecular and Cellular Biology, vol. 26(24), Dec. 23, 2006, pp. 9220-9231.

International Application No. PCT/US2012/032110, International Preliminary Report on Patentability dated Oct. 17, 2013, 9 pages.

International Application No. PCT/US2012/032110, International Search Report and Written Opinion dated Nov. 16, 2012, 12 pages.

Reimold et al., Plasma cell differentiation requires the transcription factor XBP-1, Nature 412(6844), 2001, pp. 300-307.

Rideout et al., Synergism, antagonism, and potentiation in chemotherapy: an overview, In: T.-C. Chou and D. C. Rideout (eds.), Synergism and Antagonism in Chemotherapy, Acad Press: San Diego, 1991, pp. 3-53.

Riggins et al., The NFkB inhibitor parthenolide restores ICI 182,780 (Faslodex; Fulvestrant)-induced apoptosis in antiestrogen resistant breast cancer cells, Mol Cancer Ther, vol. 4, issue 1, Jan. 2005, pp. 33-41.

Ron, Translational control in the endoplasmic reticulum stress response, J. Clin Invest, vol. 110, issue 10, Nov. 2002, pp. 1383-1388.

Shajahan et al., The Role of X-Box Binding Protein-1 in Tumorigenicity, Drug News Perspect, 22, 2009, pp. 241-246.

Shajahan et al., XBP1 and the unfolded protein response in antiestrogen resistance in breast cancer, Cancer Res., 70(8), 2010, p. 2919.

Shajahan et al., XBP-1 promotes cell survival by activating the unfolded protein response (UPR) in antiestrogen resistance in breast cancer, Cancer Research, AM2011-2070, Apr. 15, 2011, 1 Page of Abstract Only.

Shamu et al., Oligomerization and phosphorylation of the Ire1p kinase during intracellular signaling from the endoplasmic reticulum to the nucleus, EMBO, 15(2), 1996, pp. 3028-3039.

Simone, Oncology: Introduction, Cecil Textbook of Medicine, 20th Edition, vol. 1, 1996, pp. 1004-1010.

Sriburi et al., XBP1: a link between the unfolded protein response, lipid biosynthesis, and biogenesis of the endoplasmic reticulum, The Journal of Cell Biology, vol. 167, Issue 1, Oct. 2004, pp. 35-41.

Thompson et al., Evaluation of the current knowledge limitation in breast cancer research: a gap analysis, Breast endoplasmic reticulum, J Cell Biol, vol. 167, 2008, pp. 35-41.

Thorpe, Estrogen and progesterone receptor determinations in breast cancer. Technology, biology and clinical significance, Acta Oncol., 27, 1988, pp. 1-19.

Virrey et al., Stress chaperone GRP78/BiP confers chemoresistance to tumor-associated endothelial cells, Mol Cancer Res., 6, 2008, pp. 1268-1275.

Yoshida et al., XBP1 mRNA is Induced by ATF6 and Spliced by IRE1 in Response to ER Stress to Produce a Highly Active Transcription Factor, Cell, 107(7), Dec. 28, 2001, pp. 881-891.

Zhang et al., The unfolded protein response: A stress signaling pathway critical for health and disease, Neurology, vol. 66, Jan. 24, 2006, pp. S102-S109.

SMALL MOLECULE INHIBITORS OF XBP1 SPLICING

CROSS-REFERENCE TO RELATED APPLICATIONS

This application is a continuation of U.S. application Ser. No. 14/009,969, filed on Nov. 22, 2013, which is a U.S. national stage application under 35 U.S.C § 371 of PCT/US2012/032110, filed on Apr. 4, 2012, which claims the benefit of U.S. Provisional Application No. 61/471,479, filed Apr. 4, 2011. The above-listed applications are incorporated herein by reference in their entireties.

STATEMENT REGARDING FEDERALLY FUNDED RESEARCH

This invention was made with government support under grant numbers U54-CA149147 awarded by the National Institutes of Health and W81XWH-08-1-0319 awarded by the Department of Defense. The government has certain rights in the invention.

BACKGROUND

Approximately 70% of newly diagnosed breast cancer patients are estrogen receptor-α positive (ER+). However, almost 50% of all ER+ breast tumors will not respond to endocrine therapy. Tamoxifen produces an overall 26% proportional reduction in mortality but many ER+ tumors that show an initial response eventually recur. Resistance to endocrine therapy remains a significant clinical problem and advanced ER+ breast cancer is largely an incurable disease.

X-Box binding protein 1 (XBP1) is a key component of the signaling mechanism that contributes to endocrine resistance in breast cancer cells. XBP1 is a critical component of the unfolded protein response (UPR), which can act as a switch to control the balance between cell death and cell survival. UPR is induced by cellular stressors and is activated by each of three molecular sensors, including IRE1α, ATF6, and PERK. XBP1 undergoes unconventional splicing in the cytosol by IRE1α and is an obligate component in both IRE1α-induced (XBP1s) and ATF6-induced (XBP1u) arms of the UPR. IRE1α is the only ribonuclease known to date to splice XBP1.

SUMMARY

Provided herein are small molecule inhibitors of XBP1 splicing by IRE1α. Also provided herein are methods for their use in treating or preventing cancer (e.g., endocrine resistant breast cancer), diabetes, and obesity. A class of compounds described herein includes compounds of the following structure:

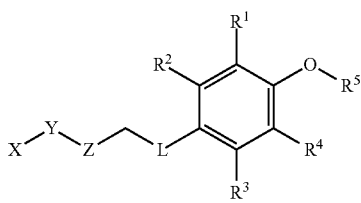

and pharmaceutically acceptable salts or prodrugs thereof. In these compounds, L is —C(=O)NH—, —NHC(=O)—, —C(=O)O—, —C(=O)—CH$_2$—,

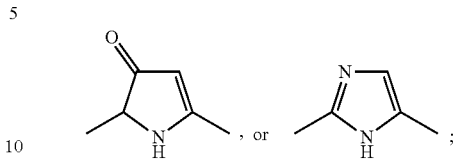

R$^1$, R$^2$, R$^3$, and R$^4$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; R$^5$ is substituted or unsubstituted aryl, substituted or unsubstituted cycloalkyl, substituted or unsubstituted alkynyl, or dansyl; X is substituted or unsubstituted aryl, substituted or unsubstituted heteroaryl, substituted or unsubstituted cycloalkyl, substituted or unsubstituted sulfonyl, or substituted or unsubstituted alkynyl; Y is substituted or unsubstituted thiazole, substituted or unsubstituted triazole, substituted or unsubstituted imidazole, substituted or unsubstituted cyclopentyl, or substituted or unsubstituted cyclopentadienyl; and Z is S, O, NH, or CH$_2$. Optionally, if Y is 1,2,4-triazole, Z is S, L is —C(=O)NH—, R$^5$ is unsubstituted phenyl, and R$^1$, R$^2$, R$^3$, and R$^4$ are each hydrogen, then X is not

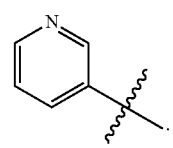 [SMILES: *c1cccnc1]

A class of compounds described herein includes compounds of the following structure:

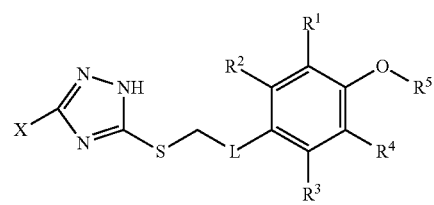

and pharmaceutically acceptable salts or prodrugs thereof. In these compounds, L is —C(=O)NH—, —NHC(=O)—, —C(=O)O—, —C(=O)—CH$_2$—,

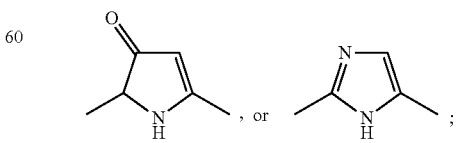

R$^1$, R$^2$, R$^3$, and R$^4$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; $R^5$ is substituted or unsubstituted aryl, substituted or unsubstituted cycloalkyl, substituted or unsubstituted alkynyl, or dansyl; and X is substituted or unsubstituted aryl, substituted or unsubstituted heteroaryl, substituted or unsubstituted cycloalkyl, substituted or unsubstituted sulfonyl, or substituted or unsubstituted alkynyl. Optionally, if L is —C(=O)NH—, $R^5$ is unsubstituted phenyl, and $R^1$, $R^2$, $R^3$, and $R^4$ are each hydrogen, then X is not

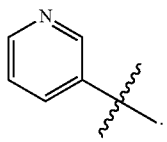 [SMILES: *c1cccnc1]

Optionally, $R^5$ is substituted or unsubstituted phenyl or fluoro-substituted phenyl. Optionally, X is pyridyl, phenyl, cyclohexyl, alkynyl, or dansyl. Optionally, L is —C(=O)NH—.

A class of compounds described herein includes compounds of the following structure:

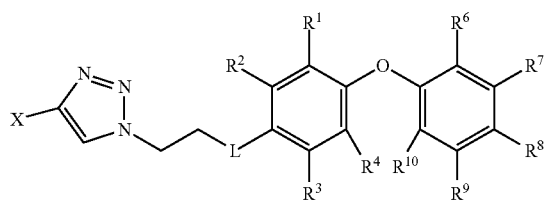

and pharmaceutically acceptable salts or prodrugs thereof. In these compounds, L is —C(=O)NH—, —NHC(=O)—, —C(=O)O—, —C(=O)—CH$_2$—,

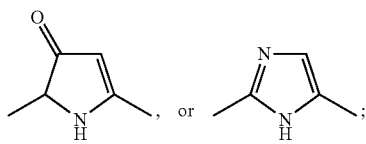

$R^1$, $R^2$, $R^3$, $R^4$, $R^6$, $R^7$, $R^8$, $R^9$, and $R^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; and X is substituted or unsubstituted heteroaryl. Optionally, X is pyridyl. Optionally, L is —C(=O)NH—.

A class of compounds described herein includes compounds of the following structure:

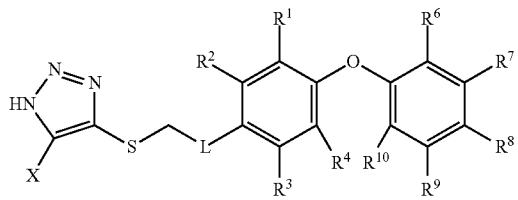

and pharmaceutically acceptable salts or prodrugs thereof. In these compounds, L is —C(=O)NH—, —NHC(=O)—, —C(=O)O—, —C(=O)—CH$_2$—,

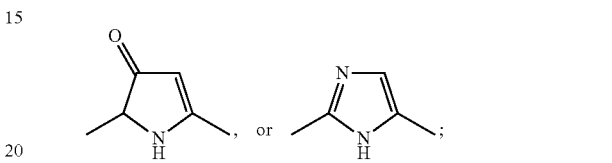

$R^1$, $R^2$, $R^3$, $R^4$, $R^6$, $R^7$, $R^8$, $R^9$, and $R^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; and X is substituted or unsubstituted heteroaryl. Optionally, X is pyridyl. Optionally, L is —C(=O)NH—.

A class of compounds described herein includes compounds of the following structure:

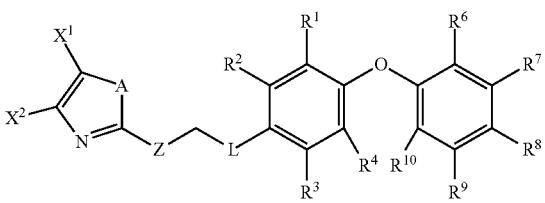

and pharmaceutically acceptable salts or prodrugs thereof. In these compounds, A is S or NH; L is —C(=O)NH—, —NHC(=O)—, —C(=O)O—, —C(=O)—CH$_2$—,

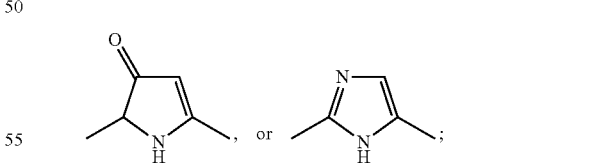

$R^1$, $R^2$, $R^3$, $R^4$, $R^6$, $R^7$, $R^8$, $R^9$, and $R^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; $X^1$ and $X^2$ are each independently selected from hydrogen, halogen, trifluoromethyl, substituted or unsubstituted alkyl, or substituted or unsubstituted heteroaryl; and Z is S or NH. Optionally, one of $X^1$ or $X^2$ is substituted or unsubstituted heteroaryl. Optionally, $X^1$ or $X^2$ is pyridyl. Optionally, L is —C(=O)NH—.

A class of compounds described herein includes compounds of the following structure:

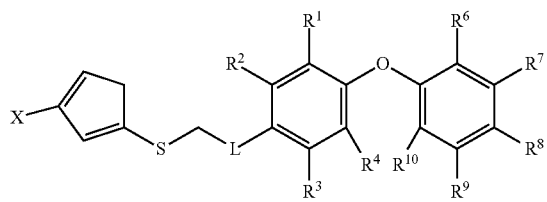

and pharmaceutically acceptable salts or prodrugs thereof. In these compounds, L is —C(=O)NH—, —NHC(=O)—, —C(=O)O—, —C(=O)—CH$_2$—,

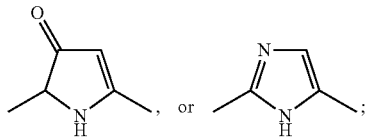

$R^1$, $R^2$, $R^3$, $R^4$, $R^6$, $R^7$, $R^8$, $R^9$, and $R^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; and X is substituted or unsubstituted heteroaryl. Optionally, X is pyridyl. Optionally, L is —C(=O)NH—.

A class of compounds described herein includes compounds of the following structure:

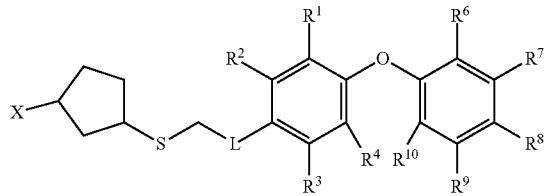

and pharmaceutically acceptable salts or prodrugs thereof. In these compounds, L is —C(=O)NH—, —NHC(=O)—, —C(=O)O—, —C(=O)—CH$_2$—,

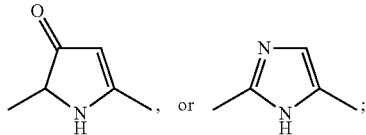

$R^1$, $R^2$, $R^3$, $R^4$, $R^6$, $R^7$, $R^8$, $R^9$, and $R^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; and X is substituted or unsubstituted heteroaryl. Optionally, X is pyridyl. Optionally, L is —C(=O)NH—.

A class of compounds described herein includes compounds of the following structure:

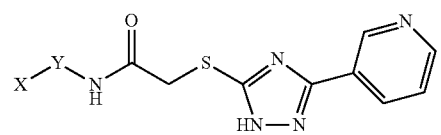

and pharmaceutically acceptable salts or prodrugs thereof. In these compounds, X is substituted or unsubstituted aryl, substituted or unsubstituted heteroaryl, substituted or unsubstituted cycloalkyl, substituted or unsubstituted sulfonyl, or substituted or unsubstituted alkynyl; and Y is substituted or unsubstituted thiazole, substituted or unsubstituted triazole, substituted or unsubstituted imidazole, or —V—CH$_2$—O—, wherein V is substituted or unsubstituted cyclohexyl, alkynyl, or substituted or unsubstituted pyridyl.

A class of compounds described herein includes compounds of the following structure:

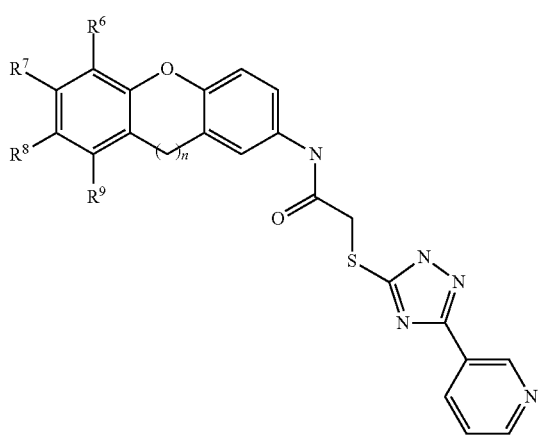

and pharmaceutically acceptable salts or prodrugs thereof. In these compounds, n is 0, 1, or 2; and $R^6$, $R^7$, $R^8$, and $R^9$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Further described herein are compounds of the following structures:

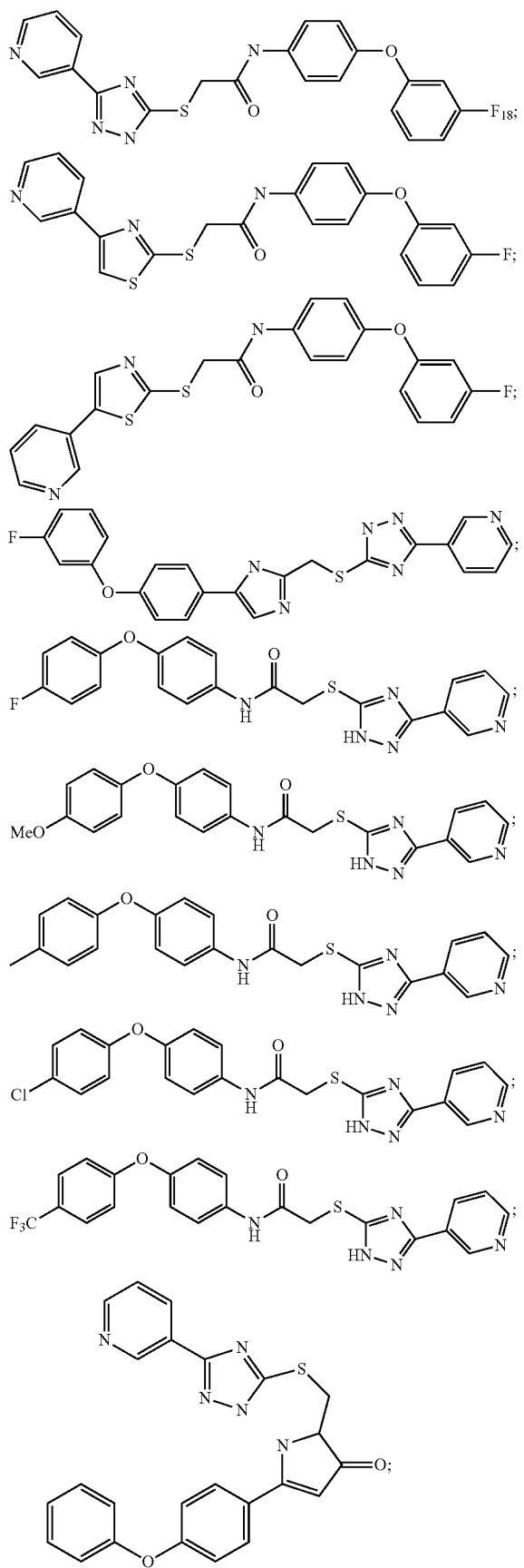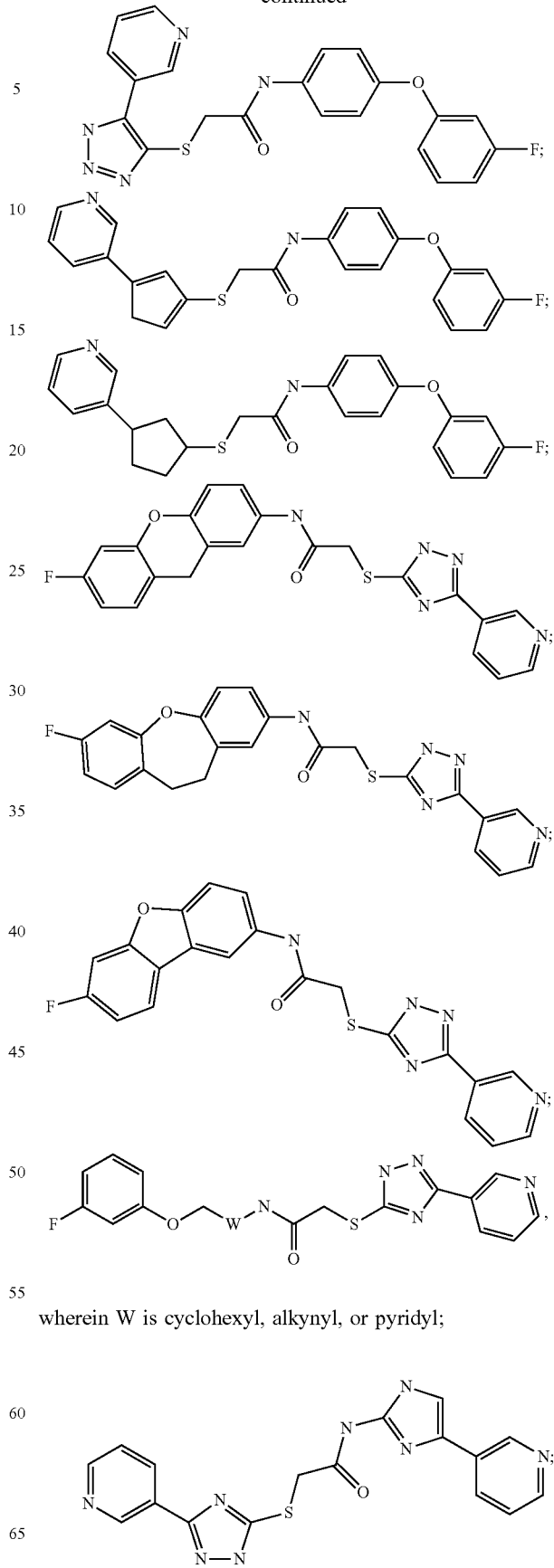
wherein W is cyclohexyl, alkynyl, or pyridyl;

-continued

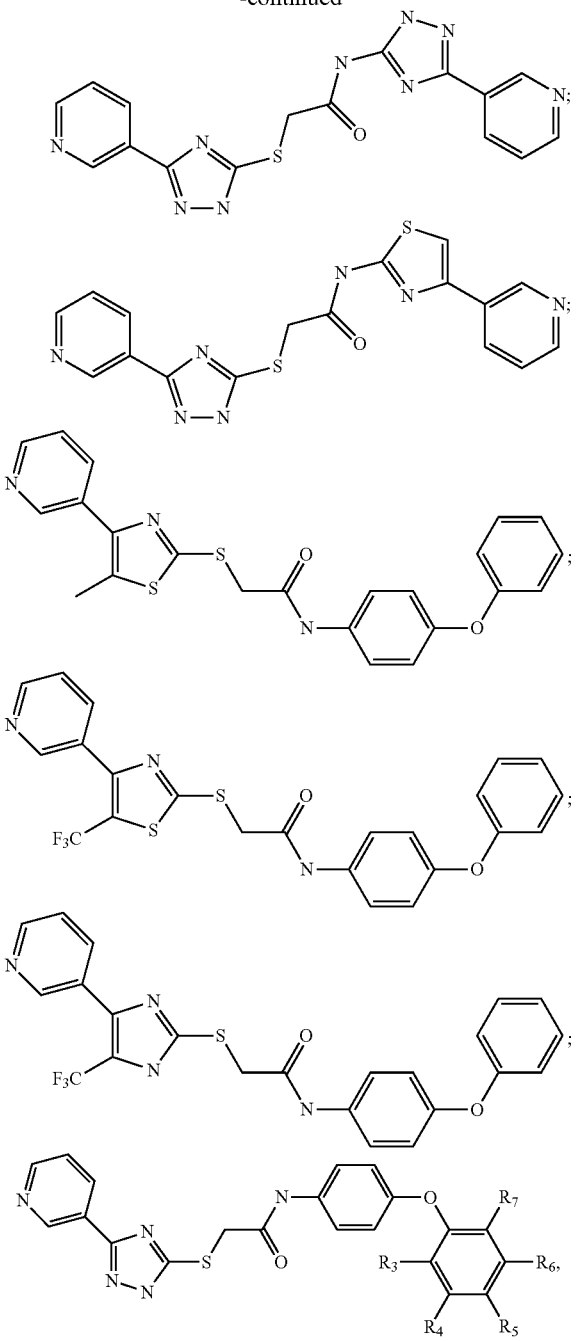

wherein $R^6$, $R^7$, $R^8$, $R^9$, and $R^{10}$ are each independently selected from hydrogen, chloro, fluoro, trifluoromethyl, hydroxyl, methoxyl, and methyl, and wherein $R^6$, $R^7$, $R^8$, $R^9$, and $R^{10}$ are not simultaneously hydrogen;

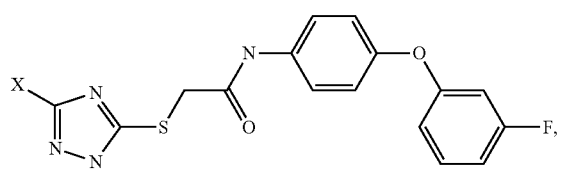

wherein X is phenyl, cyclohexyl, alkynyl, dansyl, or pyridyl; and

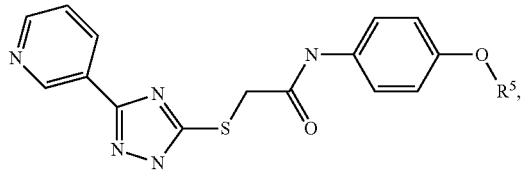

wherein $R^5$ is phenyl, cyclohexyl, alkynyl, dansyl, or pyridyl.

Also provided herein are compositions comprising one or more of the compounds described above and a pharmaceutically acceptable carrier.

Further provided herein are methods of treating or preventing cancer in a subject. A method of treating or preventing cancer in a subject includes administering to the subject an effective amount of a composition as described herein or administering to the subject an effective amount of a composition comprising a compound of the following structure:

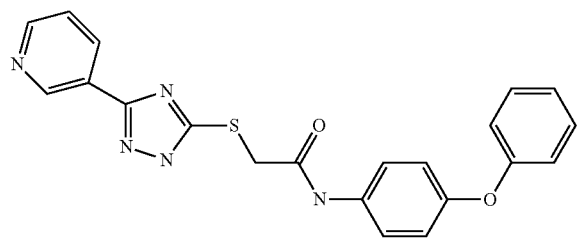 [SMILES: O=C(CSc1nc(-c2cccnc2)n[nH]1)Nc1ccc(Oc2ccccc2)cc1]

and a pharmaceutically acceptable carrier. Optionally, the cancer is breast cancer. Optionally, the breast cancer is endocrine resistant breast cancer. Optionally, the methods of treating or preventing cancer in a subject further comprise administering a second therapeutic agent, such as an antiestrogen or an aromatase inhibitor, to the subject.

Methods of treating or preventing diabetes in a subject are also provided herein. A method of treating or preventing diabetes in a subject includes administering to the subject an effective amount of a composition as described herein or administering to the subject an effective amount of a composition comprising a compound of the following structure:

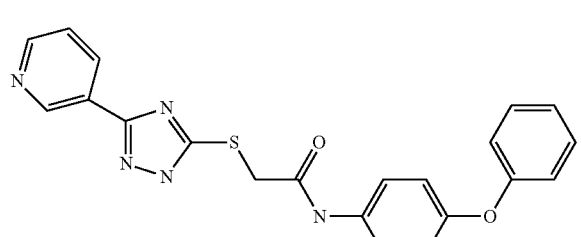

and a pharmaceutically acceptable carrier.

Also provided herein are methods of treating or preventing obesity in a subject. A method of treating or preventing obesity in a subject includes administering to the subject an effective amount of a composition as described herein or administering to the subject an effective amount of a composition comprising a compound of the following structure:

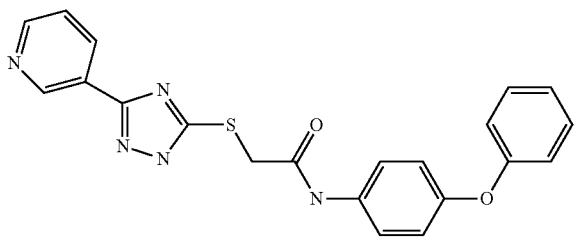 [SMILES: O=C(CSc1nc(-c2cccnc2)n[nH]1)Nc1ccc(Oc2ccccc2)cc1]

and a pharmaceutically acceptable carrier.

Further provided herein are methods of reducing XBP1 splicing or IRE1α activity in a cell as compared to a control. The methods include contacting a cell with an effective amount of one or more compounds as described herein or contacting the cell with an effective amount of a compound of the following structure:

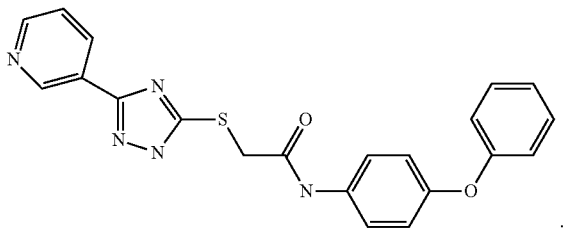

Optionally, the contacting is performed in vivo. Optionally, the contacting is performed in vitro.

Further provided herein are methods of treating a subject with anti-estrogen resistant breast cancer. The methods comprise selecting a subject with anti-estrogen resistant breast cancer; administering to the subject one or more of the compounds as described herein or a compound of the following structure:

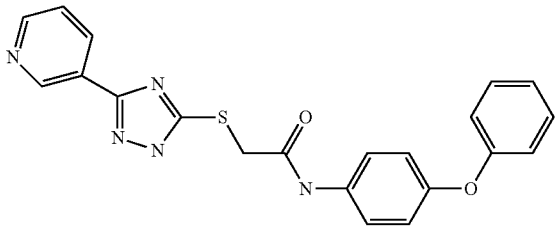 [SMILES: O=C(CSc1nc(-c2cccnc2)n[nH]1)Nc1ccc(Oc2ccccc2)cc1]

and administering to the subject an anti-estrogen compound.

The details of one or more embodiments are set forth in the drawings and the description below. Other features, objects, and advantages will be apparent from the description and drawings, and from the claims.

DETAILED DESCRIPTION

Figure 1:
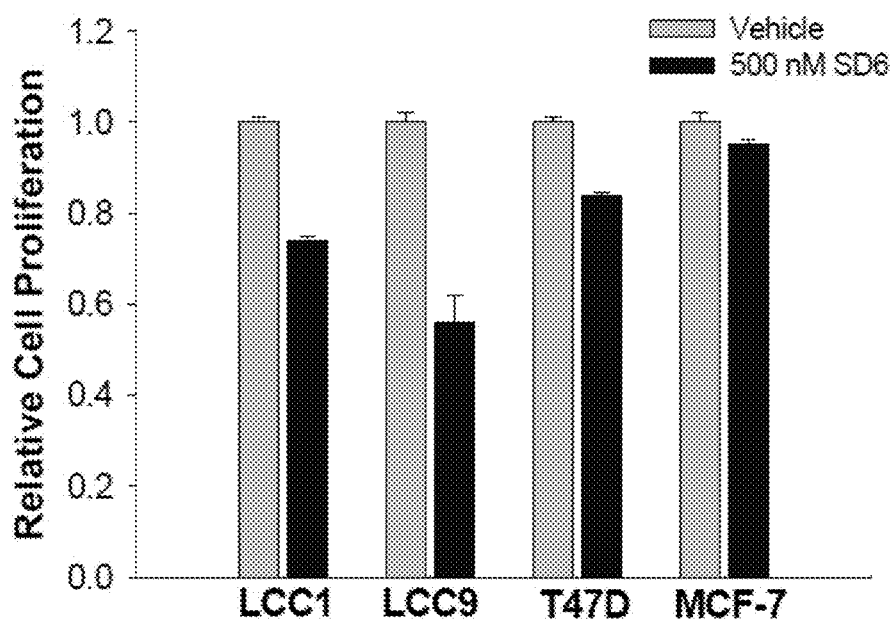
FIG. 1 is a graph showing the relative cell proliferation of different breast cancer cell lines, including MCF7/LCC1, MCF7/LCC9, T47D, and MCF-7, treated with Compound Sd-6.

Described herein are compounds for use as small molecule inhibitors of XBP1 splicing by IRE1α. Also provided herein are methods for their use in treating or preventing disorders associated with XBP1 splicing, including cancer (e.g., endocrine resistant breast cancer), diabetes, and obesity. The methods of preventing or treating cancer, diabetes, or obesity described herein include administering to the subject an XBP1 splicing inhibitor. Such inhibitors are administered in an effective amount to prevent or treat one or more symptoms of cancer, diabetes, or obesity.

I. Compounds

A class of XBP1 splicing inhibitors useful in the methods described herein includes compounds represented by Formula I:

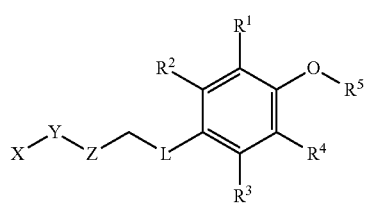

or a pharmaceutically acceptable salt or prodrug thereof.

In Formula I, L is —C(=O)NH—, —NHC(=O)—, —C(=O)O—, —C(=O)—CH$_2$—,

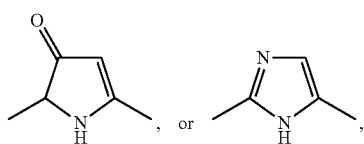

Also, in Formula I, $R^1$, $R^2$, $R^3$, and $R^4$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Additionally, in Formula I, $R^5$ is substituted or unsubstituted aryl, substituted or unsubstituted cycloalkyl, substituted or unsubstituted alkynyl, or dansyl.

Further, in Formula I, X is substituted or unsubstituted aryl, substituted or unsubstituted heteroaryl, substituted or unsubstituted cycloalkyl, substituted or unsubstituted sulfonyl, or substituted or unsubstituted alkynyl.

Also, in Formula I, Y is substituted or unsubstituted thiazole, substituted or unsubstituted triazole, substituted or unsubstituted imidazole, substituted or unsubstituted cyclopentyl, or substituted or unsubstituted cyclopentadienyl.

Additionally, in Formula I, Z is S, O, NH, or $CH_2$.

In some examples of Formula I, if Y is 1,2,4-triazole, Z is S, L is —C(=O)NH—, $R^5$ is unsubstituted phenyl, and $R^1$, $R^2$, $R^3$, and $R^4$ are each hydrogen, then X is not

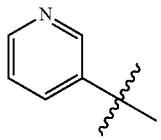

In some examples, Formula I can be represented by Formula I-A:

I-A

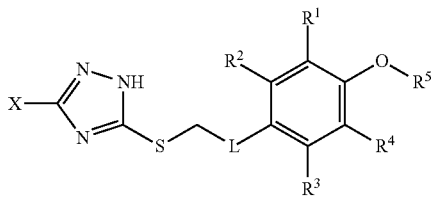

or a pharmaceutically acceptable salt or prodrug thereof.

In Formula I-A, L is —C(=O)NH—, —NHC(=O)—, —C(=O)O—, —C(=O)—$CH_2$—,

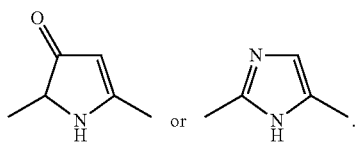

In some examples, L is —C(=O)NH—.

Also, in Formula I-A, $R^1$, $R^2$, $R^3$, and $R^4$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Additionally, in Formula I-A, $R^5$ is substituted or unsubstituted aryl, substituted or unsubstituted cycloalkyl, substituted or unsubstituted alkynyl, or dansyl. In some examples, $R^5$ is substituted or unsubstituted phenyl or fluoro-substituted phenyl.

Further, in Formula I-A, X is substituted or unsubstituted aryl, substituted or unsubstituted heteroaryl, substituted or unsubstituted cycloalkyl, substituted or unsubstituted sulfonyl, or substituted or unsubstituted alkynyl. Optionally, X is pyridyl, phenyl, cyclohexyl, alkynyl, or dansyl.

Examples of Formula I-A include the following compounds:

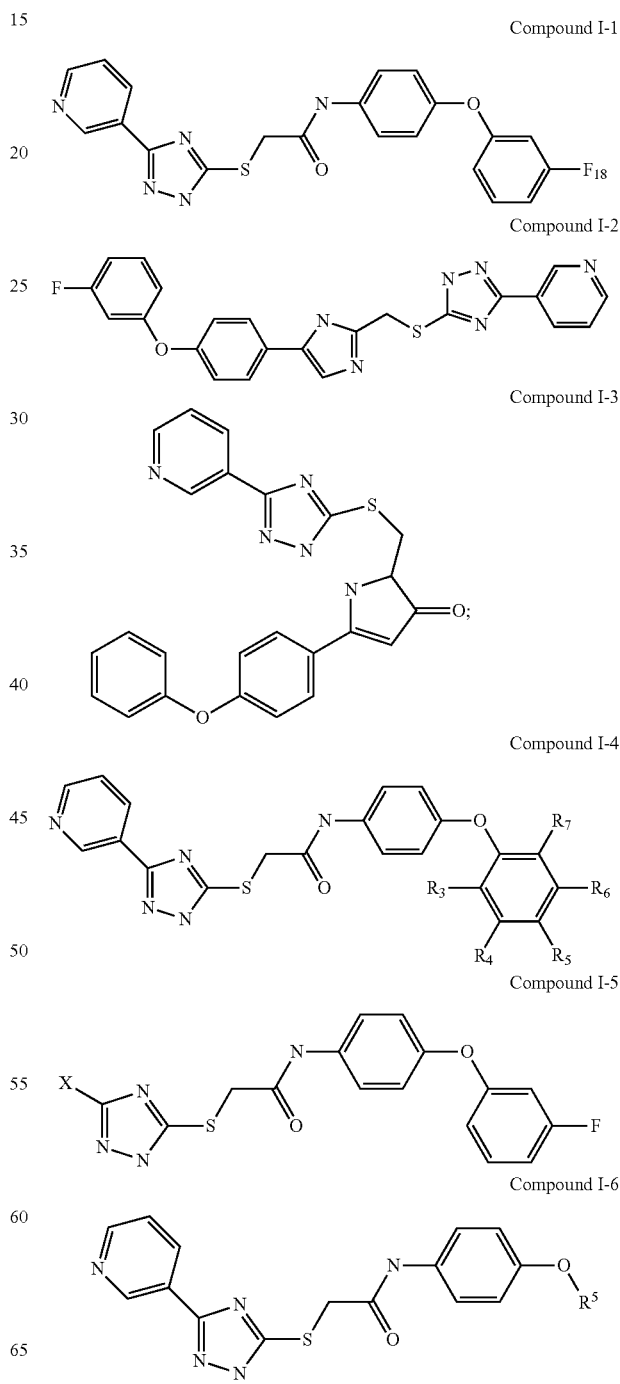

-continued

Compound I-15
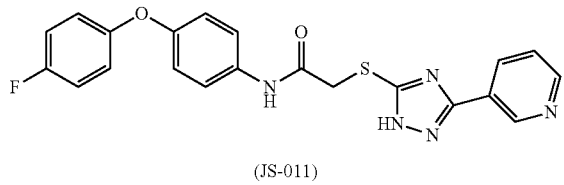
(JS-011)

Compound I-16
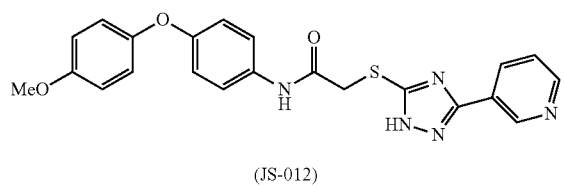
(JS-012)

Compound I-17
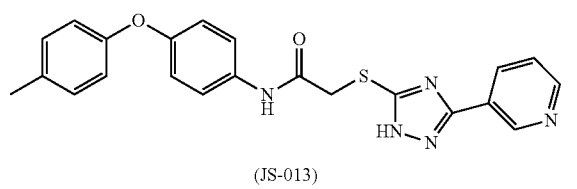
(JS-013)

Compound I-18
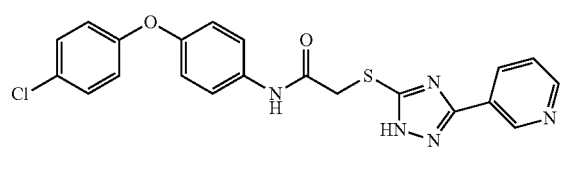
(JS-014)

Compound I-19
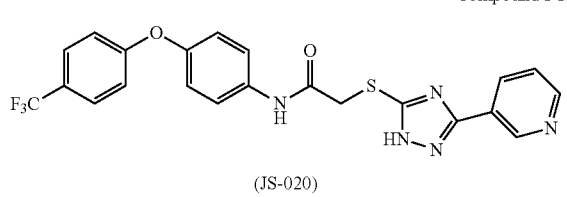
(JS-020)

In Compound I-4, $R^6$, $R^7$, $R^8$, $R^9$, and $R^{10}$ are each independently selected from hydrogen, chloro, fluoro, trifluoromethyl, hydroxyl, methoxyl, and methyl. In Compound I-4, $R^6$, $R^7$, $R^8$, $R^9$, and $R^{10}$ are not simultaneously hydrogen. In Compound I-5, X is phenyl, cyclohexyl, alkynyl, dansyl, or pyridyl. In Compound I-6, $R^5$ is phenyl, cyclohexyl, alkynyl, dansyl, or pyridyl. In some examples of Formula I-A, if L is —C(=O)NH—, $R^5$ is unsubstituted phenyl, and $R^1$, $R^2$, $R^3$, and $R^4$ are each hydrogen, then X is not

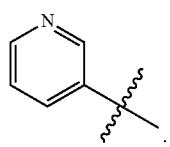 [SMILES: *c1cccnc1]

In other words, in some examples, the compound of Formula I-A is not

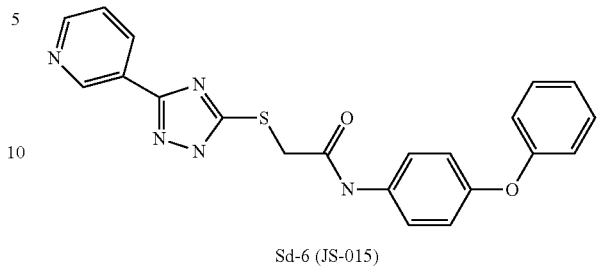

Sd-6 (JS-015)

In some examples, Formula I can be represented by Formula I-B:

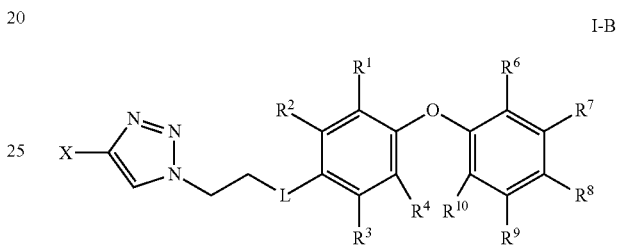

I-B or a pharmaceutically acceptable salt or prodrug thereof.

In Formula I-B, L is —C(=O)NH—, —NHC(=O)—, —C(=O)O—, —C(=O)—CH$_2$—,

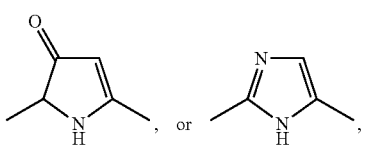

In some examples, L is —C(=O)NH—.

Also, in Formula I-B, $R^1$, $R^2$, $R^3$, $R^4$, $R^6$, $R^7$, $R^8$, $R^9$, and $R^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Additionally, in Formula I-B, X is substituted or unsubstituted heteroaryl. Optionally, X is pyridyl. In some examples, Formula I can be represented by Formula I-C:

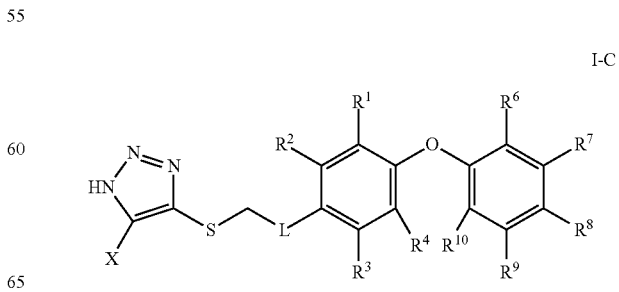

I-C or a pharmaceutically acceptable salt or prodrug thereof.

In Formula I-C, L is —C(=O)NH—, —NHC(=O)—, —C(=O)O—, —C(=O)—CH$_2$—,

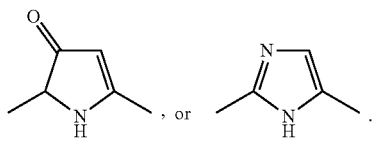, or .

Optionally, L is —C(=O)NH—.

Also, in Formula I-C, R$^1$, R$^2$, R$^3$, R$^4$, R$^6$, R$^7$, R$^8$, R$^9$, and R$^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Additionally, in Formula I-C, X is substituted or unsubstituted heteroaryl. Optionally, X is pyridyl.

An example of Formula I-C includes the following compound:

Compound I-7

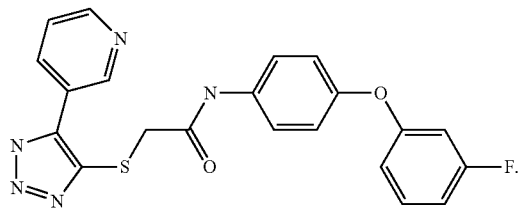

In some examples, Formula I can be represented by Formula I-D:

I-D

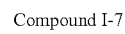

or a pharmaceutically acceptable salt or prodrug thereof.

In Formula I-D, A is S or NH.

Also in Formula I-D, L is —C(=O)NH—, —NHC(=O)—, —C(=O)O—, —C(=O)—CH$_2$—,

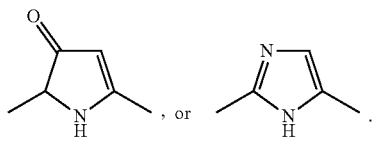, or .

In some examples, L is —C(=O)NH—.

Additionally, in Formula I-D, R$^1$, R$^2$, R$^3$, R$^4$, R$^6$, R$^7$, R$^8$, R$^9$, and R$^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Further, in Formula I-D, X$^1$ and X$^2$ are each independently selected from hydrogen, halogen, trifluoromethyl, substituted or unsubstituted alkyl, or substituted or unsubstituted heteroaryl. In Formula I-D, one of X$^1$ or X$^2$ is substituted or unsubstituted heteroaryl. In some examples, one of X$^1$ or X$^2$ is pyridyl.

Additionally, in Formula I-D, Z is S or NH.

Examples of Formula I-D include the following compounds:

Compound I-8

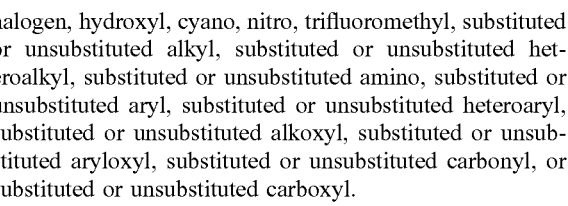

Compound I-9

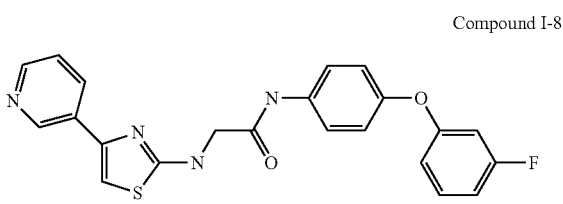

Compound I-10

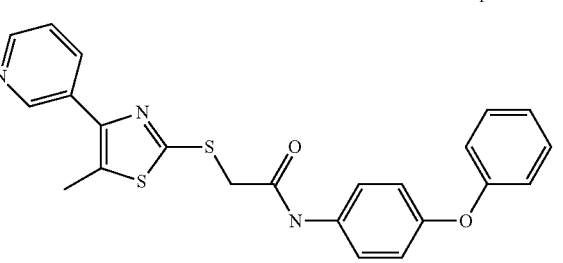

Compound I-11

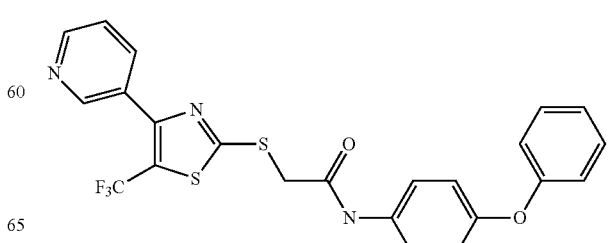

Compound I-12

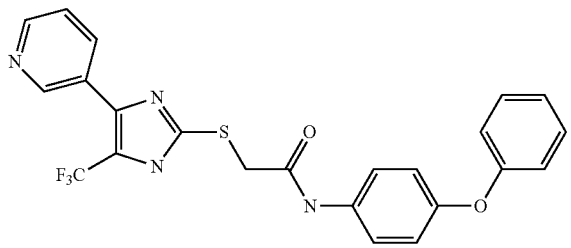

In some examples, Formula I can be represented by Formula I-E:

I-E

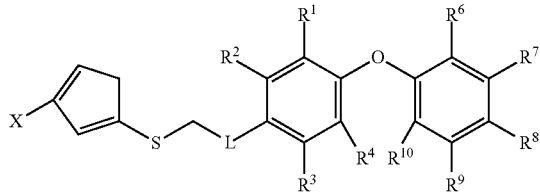

or a pharmaceutically acceptable salt or prodrug thereof.

In Formula I-E, L is —C(=O)NH—, —NHC(=O)—, —C(=O)O—, —C(=O)—CH₂—,

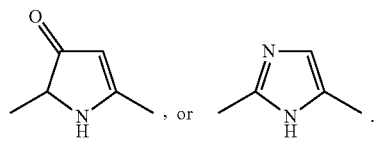, or

Optionally, L is —C(=O)NH—.

Also, in Formula I-E, $R^1$, $R^2$, $R^3$, $R^4$, $R^6$, $R^7$, $R^8$, $R^9$, and $R^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Additionally, in Formula I-E, X is substituted or unsubstituted heteroaryl. In some examples, X is pyridyl.

An example of Formula I-E includes the following compound:

Compound I-13

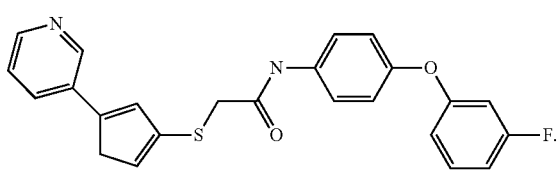

In some examples, Formula I can be represented by Formula I-F:

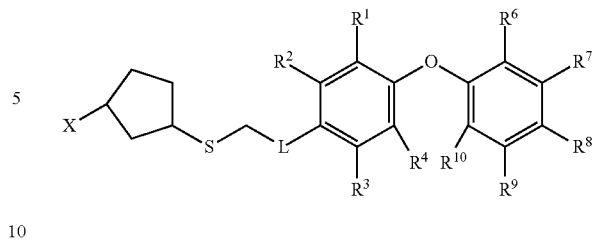

or a pharmaceutically acceptable salt or prodrug thereof.

In Formula I-F, L is —C(=O)NH—, —NHC(=O)—, —C(=O)O—, —C(=O)—CH₂—,

, or .

Optionally, L is —C(=O)NH—.

Also, in Formula I-F, $R^1$, $R^2$, $R^3$, $R^4$, $R^6$, $R^7$, $R^8$, $R^9$, and $R^{10}$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Further, in Formula I-F, X is substituted or unsubstituted heteroaryl. Optionally, X is pyridyl.

An example of Formula I-F includes the following compound:

Compound I-14

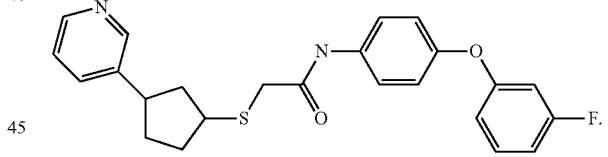

A class of XBP1 splicing inhibitors useful in the methods described herein includes compounds represented by Formula II:

II

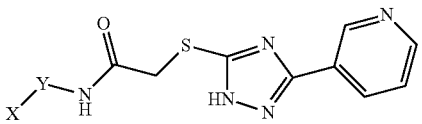

or a pharmaceutically acceptable salt or prodrug thereof.

In Formula II, X is substituted or unsubstituted aryl, substituted or unsubstituted heteroaryl, substituted or unsubstituted cycloalkyl, substituted or unsubstituted sulfonyl, or substituted or unsubstituted alkynyl.

Also, in Formula II, Y is substituted or unsubstituted thiazole, substituted or unsubstituted triazole, substituted or unsubstituted imidazole, or —V—CH₂—O—, wherein V is substituted or unsubstituted cyclohexyl, alkynyl, or substituted or unsubstituted pyridyl.

Examples of Formula II include the following compounds:

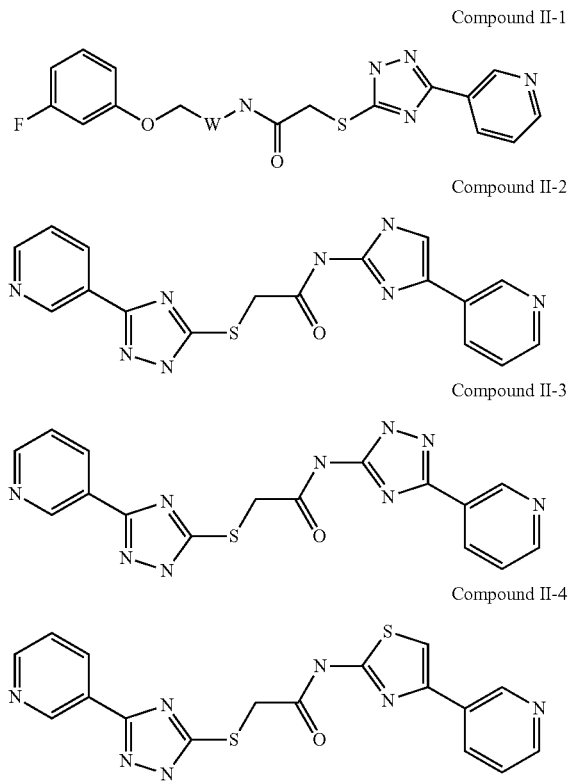

In Compound II-1, W is cyclohexyl, alkynyl, or pyridyl.

A class of XBP1 splicing inhibitors useful in the methods described herein includes compounds represented by Formula III:

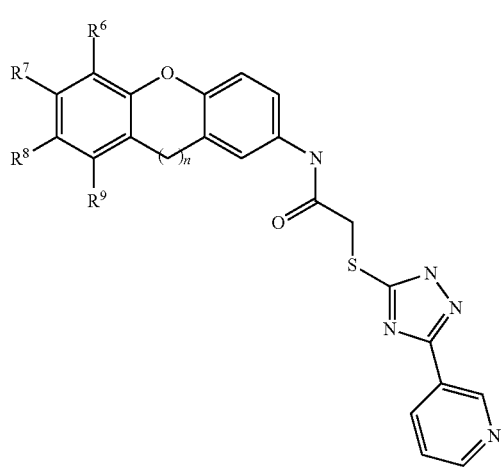

or a pharmaceutically acceptable salt or prodrug thereof.

In Formula III, n is 0, 1, or 2.

Also, in Formula III, $R^6$, $R^7$, $R^8$, and $R^9$ are each independently selected from hydrogen, halogen, hydroxyl, cyano, nitro, trifluoromethyl, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Examples of Formula III include the following compounds:

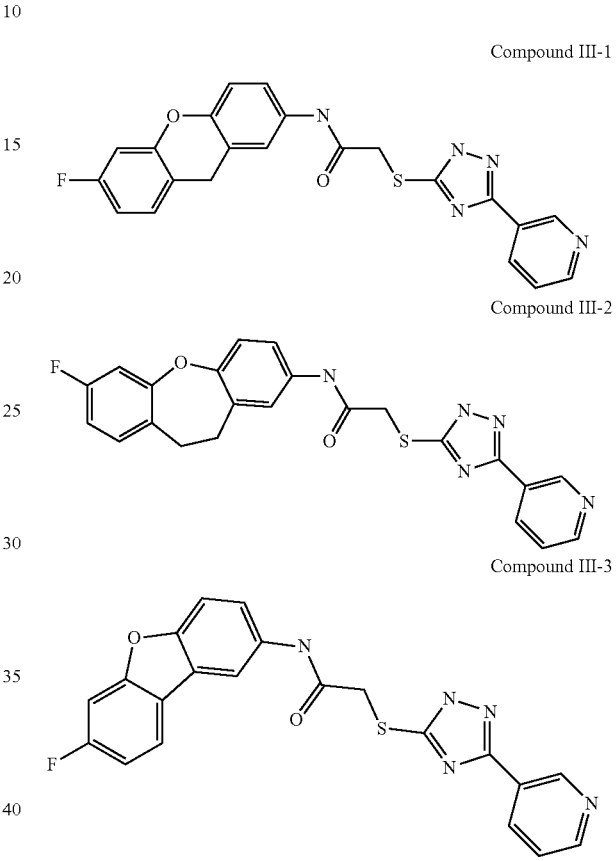

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl molecules used herein can be substituted or unsubstituted. As used herein, the term substituted includes the addition of an alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl group to a position attached to the main chain of the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl has a full complement of hydrogens, i.e., commensurate with its saturation level, with no substitutions, e.g., linear decane (—$CH_2$)$_9$—$CH_3$).

II. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

III. Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I, Formula II, and Formula III include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

The compounds described by Formula I can be made, for example, using reactions known to those of skill in the art according to the retrosynthetic methods shown in Schemes 1-5:

Scheme 1

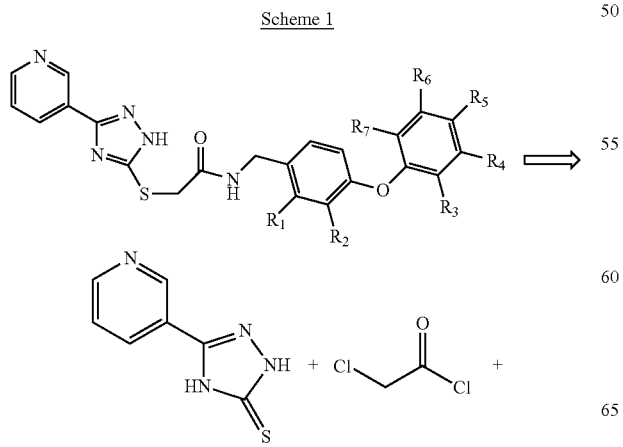

-continued

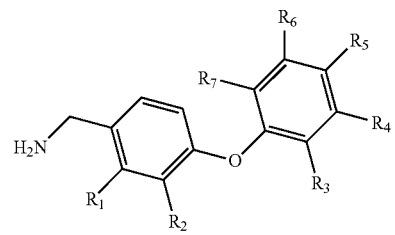

Scheme 2

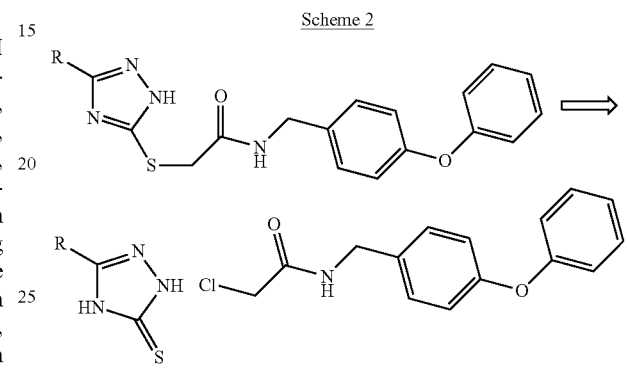

Scheme 3

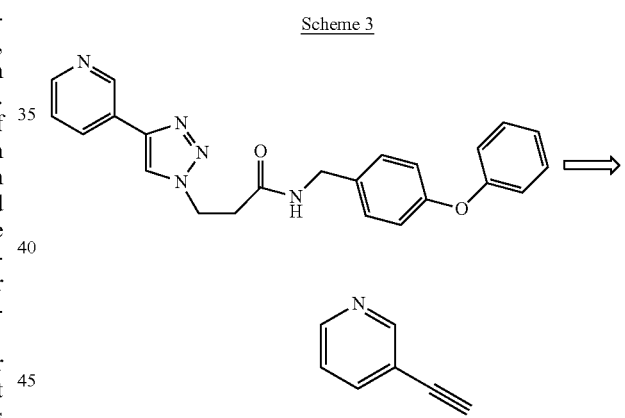

Scheme 4

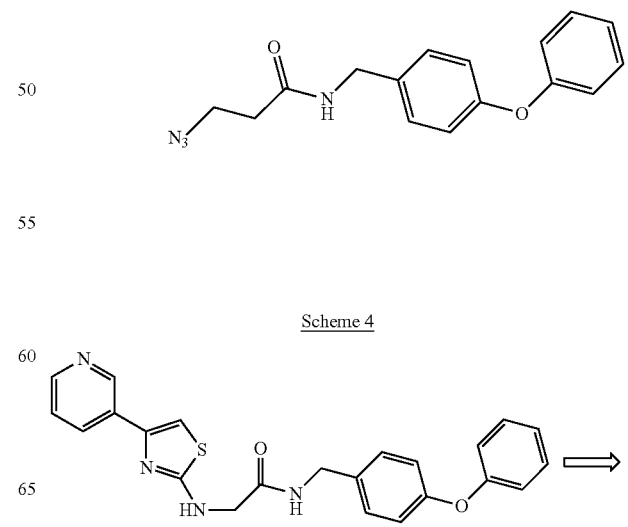

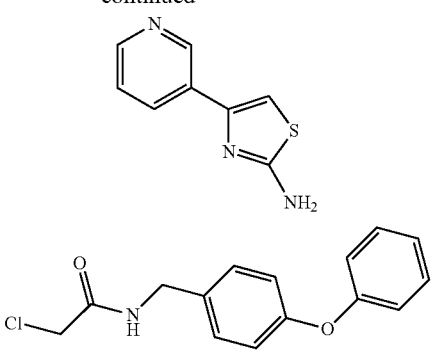

Scheme 5

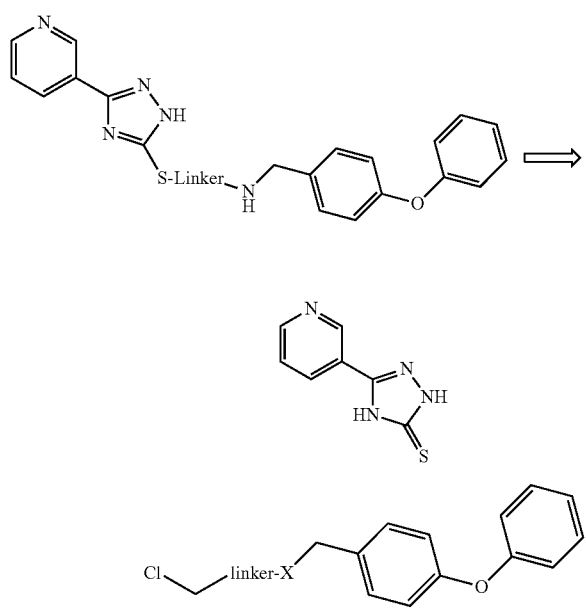

Compound Sd-6 can be synthesized according to the method shown in Scheme 6:

Scheme 6

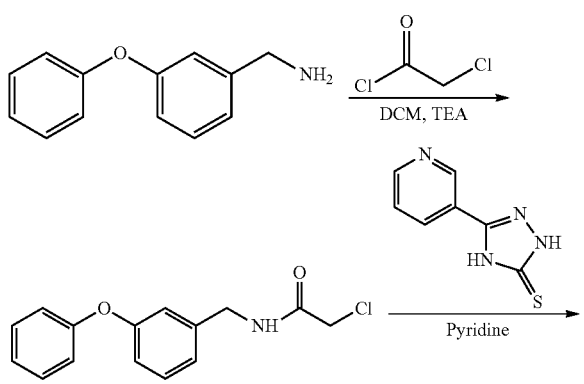

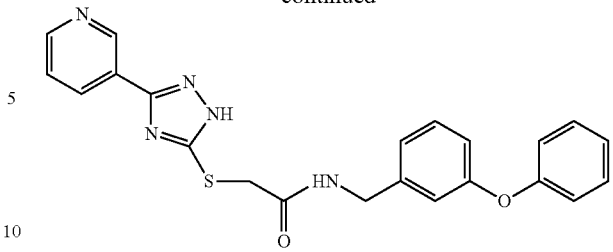

IV. Methods of Use

Provided herein are methods to treat, prevent, or ameliorate cancer, diabetes, and obesity in a subject. The methods include administering to a subject an effective amount of one or more of the compounds or compositions described herein, or a pharmaceutically acceptable salt or prodrug thereof. The expression "effective amount," when used to describe an amount of compound in a method, refers to the amount of a compound that achieves the desired pharmacological effect or other effect, for example, an amount that results in tumor growth rate reduction. The compounds and compositions described herein or pharmaceutically acceptable salts thereof are useful for treating cancer, diabetes, and obesity in humans, including, without limitation, pediatric and geriatric populations, and in animals, e.g., veterinary applications. Optionally, the cancer is breast cancer. Optionally, the breast cancer is endocrine resistant breast cancer.

Further described herein is a method of treating a subject with anti-estrogen resistant breast cancer. The method includes the steps of selecting a subject with anti-estrogen resistant breast cancer; administering to the subject one or more of the compounds as described herein; and administering to the subject an anti-estrogen compound. Anti-estrogen compounds include, without limitation, tamoxifen (NSC-180973; ICI-46474), nafoxidine, nitromifene (CI-628), and clomiphene citrate.

The methods of treating or preventing cancer, diabetes, and obesity in a subject can further comprise administering to the subject a therapeutic agent or radiation therapy or a combination thereof. Thus, the provided compositions and methods can include one or more additional agents. The one or more additional agents and the compounds described herein or pharmaceutically acceptable salts or prodrugs thereof can be administered in any order, including concomitant, simultaneous, or sequential administration. Sequential administration can be temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include, but are not limited to, chemotherapeutic agents, anti-depressants, anxiolytics, antibodies, antivirals, steroidal and non-steroidal anti-inflammatories, conventional immunotherapeutic agents, cytokines, chemokines, and/or growth factors. Therapeutic agents also include insulin and agents (e.g., Glyburide, exenatide, pramlinitide, and metformin) used to control blood sugar in subjects with diabetes and anti-obesity medications (e.g., orlistat, sibutramine, and rimonabant).

The therapeutic agent can, for example, be a chemotherapeutic agent. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, antiestrogens (e.g., Tamoxifen or Faslodex) and aromatase inhibitors (e.g., Letrozole).

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of cancer, diabetes, or obesity), during early onset (e.g., upon initial signs and symptoms of cancer, diabetes, or obesity), or after the development of cancer, diabetes, or obesity. Prophylactic administration can occur for several days to years prior to the manifestation of symptoms of cancer, diabetes, or obesity. Therapeutic treatment involves administering to a subject a therapeutically effective amount of the compounds and compositions or pharmaceutically acceptable salts thereof as described herein after cancer, diabetes, or obesity is diagnosed.

The methods and compounds described herein are also useful in reducing XBP1 splicing or IRE1α activity in a cell as compared to a control. The methods include contacting a cell with an effective amount of one or more compounds as described herein. Optionally, the contacting is performed in vivo. Optionally, the contacting is performed in vitro.

The methods herein for prophylactic and therapeutic treatment optionally comprise selecting a subject with or at risk of developing cancer, diabetes, or obesity. A skilled artisan can make such a determination using, for example, a variety of prognostic and diagnostic methods, including, for example, a personal or family history of the disease or condition, clinical tests (e.g., imaging, biopsy, genetic tests and the like for cancer; measurements of body weight or body fat for obesity and diabetes; blood glucose levels for diabetes), and the like.

V. Kits

Also provided herein are kits for treating or preventing cancer, diabetes, or obesity in a subject. A kit can include any of the compounds or compositions described herein. For example, a kit can include a compound of Formula I, Formula II, Formula III, or combinations thereof. A kit can further include one or more additional agents, such as antiestrogens (e.g., Tamoxifen or Faslodex) or aromatase inhibitors (e.g., Letrozole). A kit can include an oral formulation of any of the compounds or compositions described herein. A kit can additionally include directions for use of the kit (e.g., instructions for treating a subject), a container, a means for administering the compounds or compositions, and/or a carrier.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1

Compound Sd-6 was tested in a dose-response assay using different breast cancer cell lines, including MCF7/LCC1, MCF7/LCC9, T47D, and MCF-7. MCF7/LCC1 is an ERα-positive estrogen-independent, antiestrogen-responsive breast cancer cell line. MCF7/LCC9 is an ERα-positive estrogen-independent, antiestrogen-resistant breast cancer cell line. MCF- is an ERα-positive estrogen-dependent, antiestrogen-responsive breast cancer cell line. Cells were first plated in 96-well plastic tissue culture plates (10,000 cells per well). The cells were treated with 500 nM of Compound Sd-6 or the vehicle alone (DMSO) for 48 h. Following treatment, the cells were washed with PBS, stained with a crystal violet staining solution, and allowed to dry for 48-72 hrs. After drying, sodium citrate buffer was added to each well and allowed to incubate for 5 min at room temperature. The absorbance was measured at 450 nM using a microplate reader (Biorad; Hercules, Calif.). The relative cell proliferation for each of the breast cancer cell lines is shown in FIG. 1.

Example 2

Figure 2:
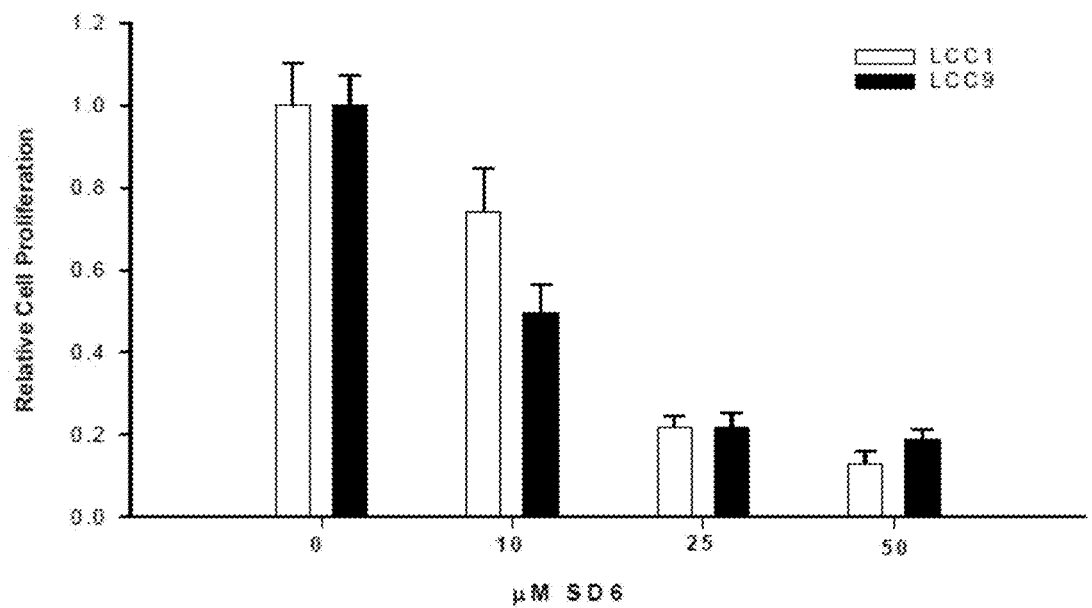
FIG. 2 is a graph showing the relative cell proliferation of MCF7/LCC1 and MCF7/LCC9 breast cancer cell lines treated with different concentrations of Compound Sd-6 (0 µM, 10 µM, 25 µM, and 50 µM).

Compound Sd-6 was tested in a dose-response assay using MCF7/LCC1 antiestrogen-responsive breast cancer cells and MCF7/LCC9 antiestrogen-resistant breast cancer cells. MCF7/LCC1 or MCF7/LCC9 cells were first plated in 96-well plastic tissue culture plates (10,000 cells per well). The cells were treated with vehicle alone (DMSO), 10 µM, 25 µM or 50 µM SD6 for 72 h. Following treatment, cell proliferation was determined using a crystal violet assay as described in Example 1. The relative cell proliferation at each concentration is shown in FIG. 2.

Example 3

Figure 3:
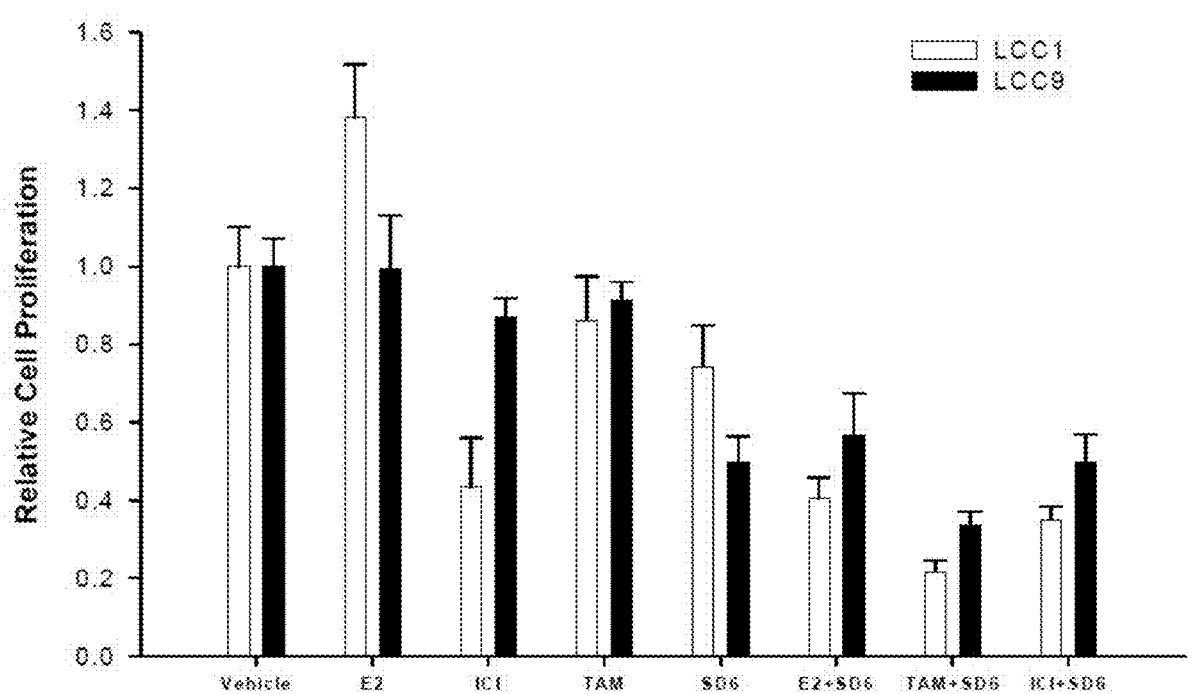
FIG. 3 is a graph showing the relative cell proliferation of MCF7/LCC1 and MCF7/LCC9 breast cancer cell lines treated with either vehicle alone (DMSO), 10 nM estradiol (E2), 100 nM Tamoxifen (TAM), 100 nM Faslodex/ICI 182,780 (ICI), or 10 µM Compound Sd-6 alone or a combination of Compound Sd-6 with E2, TAM or ICI.

Compound Sd-6 was tested in a dose-response assay using MCF7/LCC1 antiestrogen-responsive breast cancer cells and MCF7/LCC9 antiestrogen-resistant breast cancer cells. Cells were first plated in 96-well plastic tissue culture plates (10,000 cells per well). The cells were treated with either vehicle alone (DMSO), 10 nM estradiol (E2), 100 nM Tamoxifen (TAM), 100 nM Faslodex/ICI 182,780 (ICI), or 10 µM Compound Sd-6 alone or a combination of Compound Sd-6 with E2, TAM or ICI for 72 h. Following treatment, cell proliferation was determined using a crystal violet assay as described above. RI values were obtained by calculating the expected cell survival (Sexp; the product of survival obtained with drug A alone and the survival obtained with drug B alone) and dividing Sexp by the observed cell survival in the presence of both drugs (Sobs). Sexp/Sobs>1.0 indicates a synergistic interaction. In the MCF7/LCC1 cell line, ICI and Compound Sd-6 synergistically inhibited cell proliferation, showing a RI value of 1.44. Also, TAM and Compound Sd-6 synergistically inhibited cell proliferation in the MCF7/LCC1 cell line, with an RI value of 1.82. In the MCF7/LCC9 cell line, ICI and Compound Sd-6 were found to synergistically inhibit cell proliferation with an RI value of 1.27. A plot showing the relative cell proliferations is in FIG. 3.

Example 4

Figure 4:
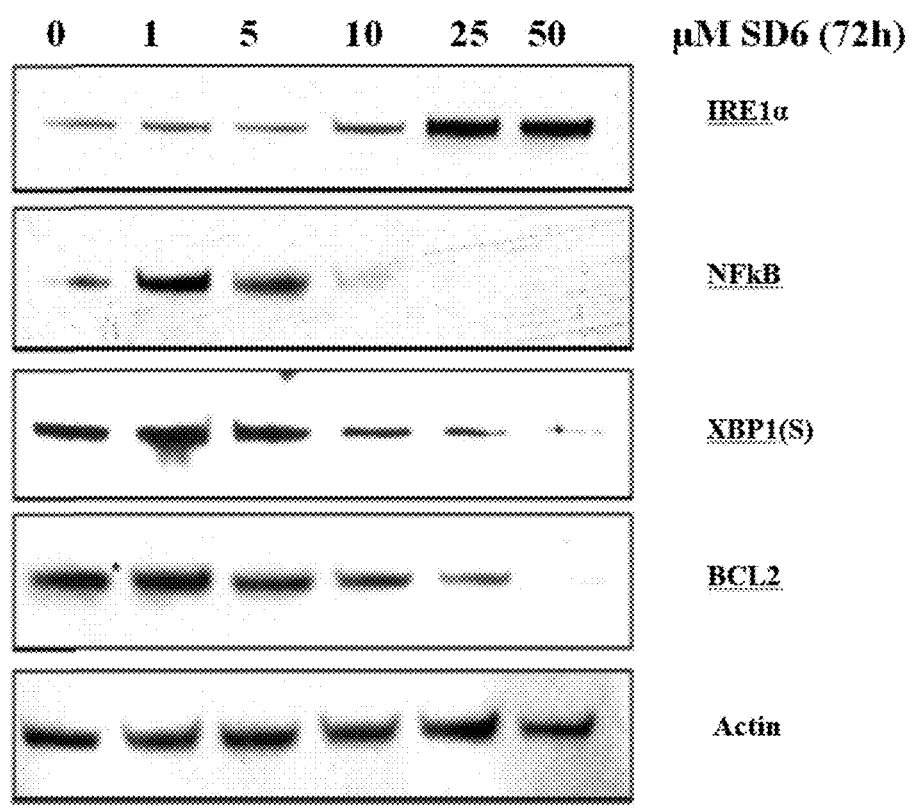
FIG. 4 is a picture of a Western Blot showing the effects of Compound Sd-6 on IRE1α, XBP1(S), NFκB (p65), BCL2, and actin primary antibodies.

Compound Sd-6 was tested for its ability to inhibit XBP1 protein expression in MCF7/LCC9 antiestrogen-resistant breast cancer cells. Cells were grown in 6-well tissue culture plates before lysis. To determine the effects of Compound Sd-6 on protein expression, cells were treated with vehicle alone (DMSO) or 1 µM, 5 µM, 10 µM, 25 µM, or 50 µM Compound Sd-6 for 72 hours. Cells were then lysed in RIPA buffer [150 mmol/L NaCl, 50 mmol/L Tris (pH 7.5), 1% Igepal CA-630, and 0.5% deoxycholate] supplemented with Complete Mini protease inhibitor cocktail tablets (Roche) and 1 mmol/L sodium orthovanadate phosphatase inhibitor (Sigma; St. Louis, Mo.). Approximately 25 µg of protein (total protein) was isolated from cell populations and size fractionated by electrophoresis using Invitrogen NuPage 10% of 12% Bis-Tris gels. Proteins were then transferred onto nitrocellulose membranes and blocked in a solution of TBS/0.1% Tween-20 (TBST), pH 7.4, and blocked in a milk solution (nonfat cow's milk diluted to 10% in TBST) for 30 minutes with constant agitation. After blocking, the nitrocellulose membrane was washed with TBST (3× for 15 minutes) and incubated with IRE1α, XBP1(S), NFκB (p65), BCL2 or actin (for loading control) primary antibodies overnight at 4° C. The membranes were then washed with TBST (3× for 15 minutes) and incubated for 1 hour in anti-mouse or anti-rabbit horseradish peroxidase-conjugated IgG (Amersham Biosciences, Piscataway, N.Y.) at a 1:5000 dilution (room temperature). Following final washes of the membrane in TBST, antigen-antibody complexes were visualized using the ECL detection system (Amersham Biosciences) and SuperSignal Chemiluminescent Substrate (Thermoscientific). The results are shown in FIG. 4.

Example 5

Figure 5:
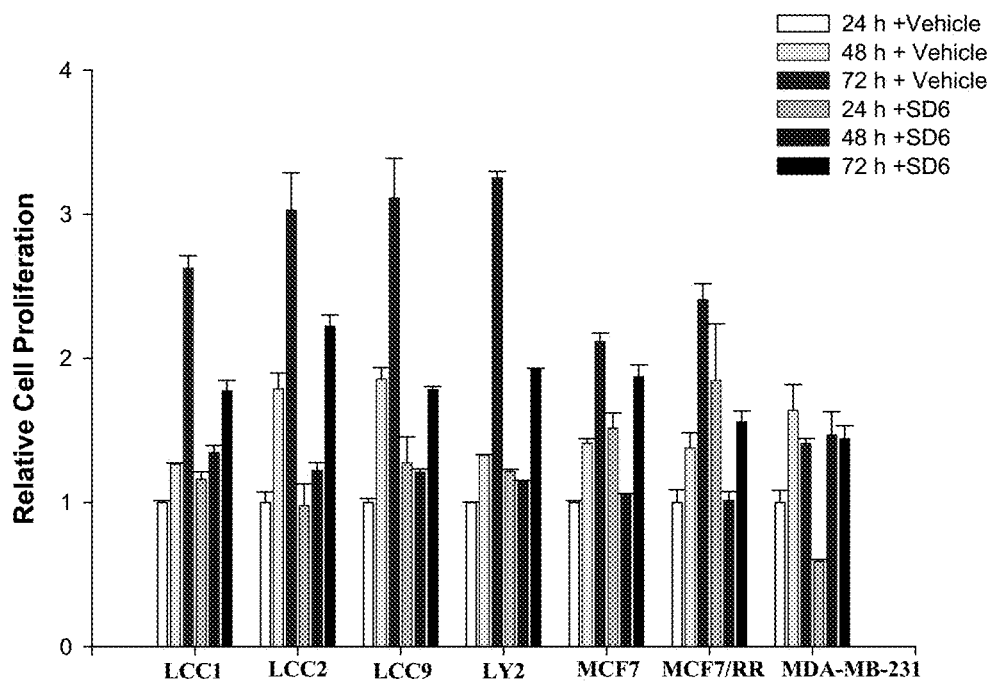
FIG. 5 is a bar graph showing the relative cell proliferation of different breast cancer cell lines treated with Compound Sd-6 at 24, 48, and 72 hours after treatment.
Figure 6:
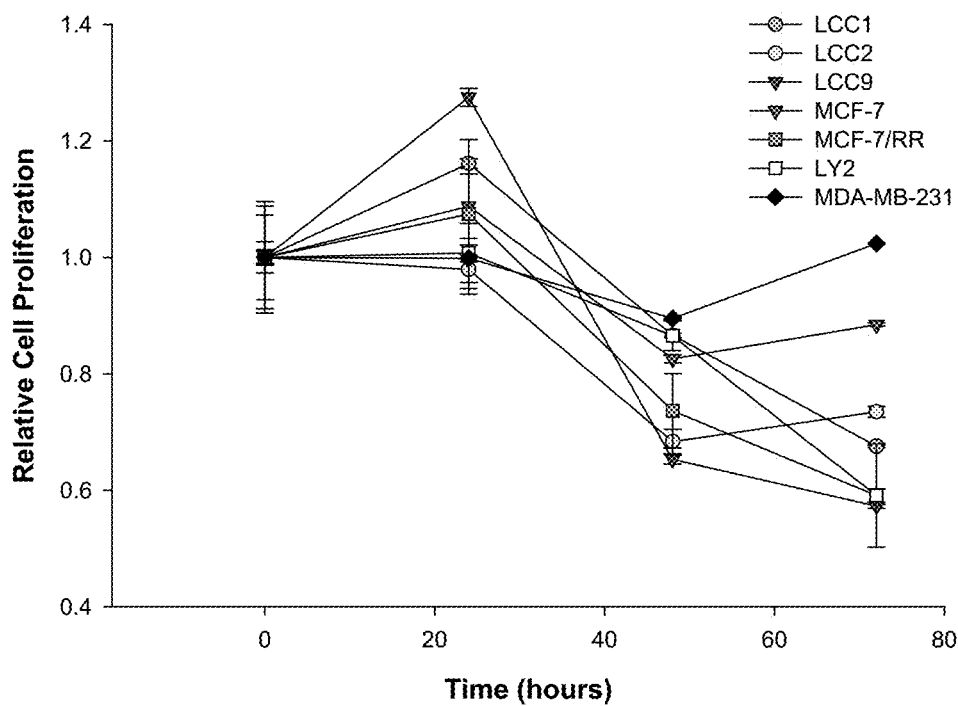
FIG. 6 is a line graph showing the relative cell proliferation of different breast cancer cell lines treated with Compound Sd-6 at 24, 48, and 72 hours after treatment.

Compound Sd-6 (10 µM) was tested in a time-course assay using different breast cancer cell lines, including MCF7/LCC1, MCF7/LCC2, MCF7/LCC9, LY2, MCF-7, MCF7/RR, and MDA-MB-231. The time points shown include 24 hours, 48 hours, and 72 hours. The vehicle is shown as well as a control. All cells were grown in DMEM phenol-free media supplemented with charcoal-stripped calf serum. The results are shown in FIGS. 5 and 6.

Example 6

Xenograft model of breast cancer: Breast cancer epithelial cells are suspended in a solution of Matrigel (BD, Franklin Lakes, N.J.) 50% v/v in PBS. Each 6-week-old NCr nu/nu mouse is inoculated with $5 \times 10^6$ cells subcutaneously into the mammary fat pad. MCF-7 cells require estrogen to grow, and therefore, 17β-estradiol pellets (0.72 mg, 60-day release; Innovative Research of America, Sarasota, Fla.) are implanted subcutaneously. Drug exposure begins when tumors reach ~60 mm$^3$. The mice of each strain are treated with Compound Sd-6 (100 mg/kg) by infusion subcutaneously and weekly for 8 weeks. Control animals are treated with a vehicle control (0.2% DMSO). Tumor measurements are made daily for 3 weeks after the first dose. Tumor volume is calculated (formula: volume=π(short diameter$^2$× (long diameter)/6) and unpaired two-sample t-test is used to test the differences in tumor size between the control and drug-treated groups. Tumor samples are collected for immunohistochemistry and Western blot analyses to detect, for example, XBP1 and IRE1α.

Example 7

Obesity/Diabetes model: C57Bl/6 mice on high-fat or control diet is given Compound Sd-6 (100 mg/kg) subcutaneously for 8 weeks. Body weight, blood glucose, and food/water intake is measured weekly. Glucose Tolerance Test (GTT) is performed at the beginning and end of treatment at 0, 30, 60, 90, and 120 min. Insulin is measured at the beginning and end of treatment. In addition, serum triglycerides, total cholesterol, and free fatty acid levels are determined at the end of treatment. Various tissue samples are collected and analyzed.

Example 8

Figure 7:
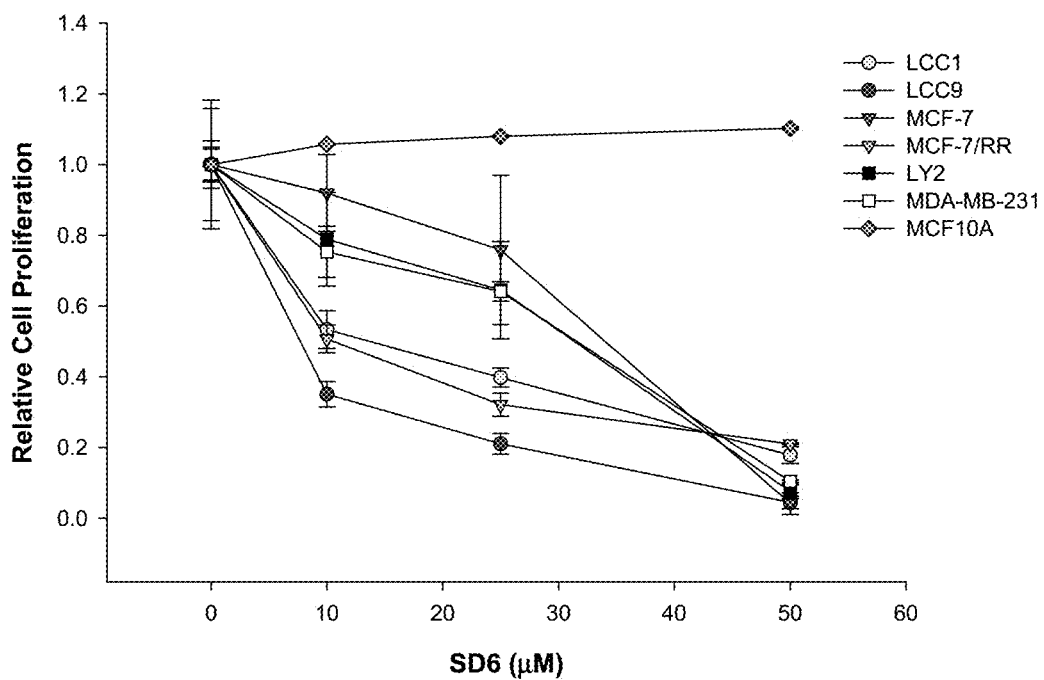
FIG. 7 is a line graph showing the relative cell proliferation of different breast cancer cell lines (MCF7/LCC1, MCF7/LCC9, T47D, MCF-7, MCF-7/RR, LY2, and MDA-MB-231) and one non-breast cancer control cell line (MCF 10A) treated with different concentrations of Compound Sd-6 (0 µM, 10 µM, 25 µM, and 50 µM).

Compound Sd-6 was tested in a dose-response assay using different breast cancer cell lines, including MCF7/LCC1, MCF7/LCC9, T47D, MCF-7, MCF-7/RR, LY2, and MDA-MB-231. MCF 10A, a non-breast cancer cell line, served as the control. The cells were first plated in 96-well plastic tissue culture plates (10,000 cells per well). The cells were treated with vehicle alone (DMSO), 10 µM, 25 µM or 50 µM SD6 for 72 h. Following treatment, cell proliferation was determined using a crystal violet assay as described in Example 1. The relative cell proliferation at each concentration is shown in FIG. 7. The MCF 10A cells did not respond to Compound Sd-6.

Example 9

Figure 8:
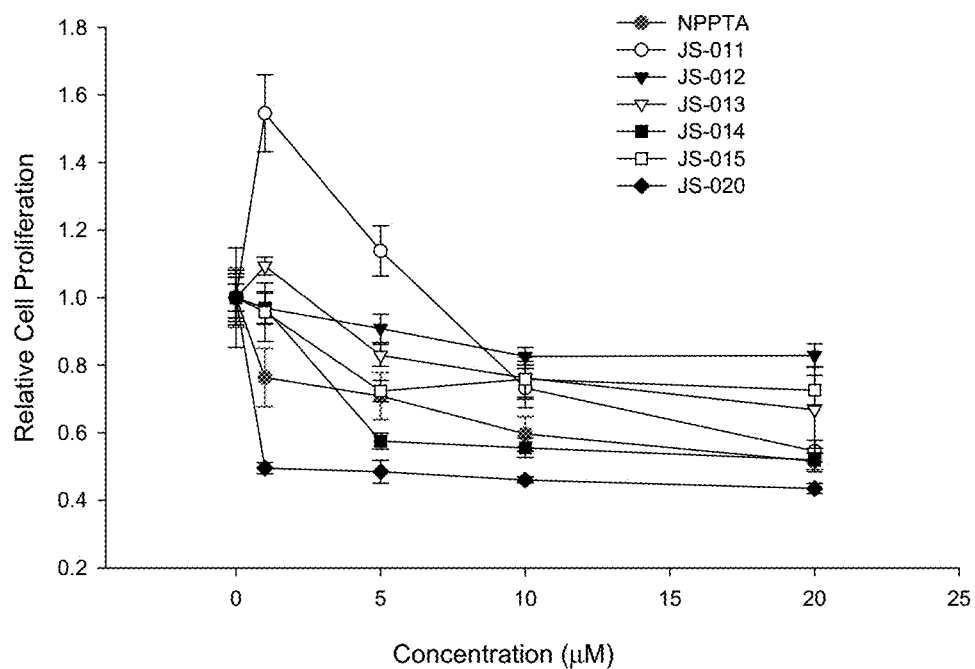
FIG. 8 is a line graph showing the relative cell proliferation of antiestrogen resistant LCC9 cell line treated with different concentrations of Compound JS-011, Compound JS-012, Compound JS-013, Compound JS-014, Compound JS-015, Compound JS-020, and NPPTA.

To measure cell viability, antiestrogen resistant LCC9 cells were plated in 96-well plastic tissue culture plates at a density of 5×10³ cells/well. Twenty-four hours after plating, cells were treated with 3-naphthoyl-1,1,1-trifluoroacetone (NPPTA) and the analogs (i.e., Compound JS-011, Compound JS-012, Compound JS-013, Compound JS-014, Compound JS-015, Compound JS-020). After 72 hours, the cell culture media was removed and plates were stained with 100 mL/well of a solution containing 0.5% crystal violet and 25% methanol, rinsed with deionized water, dried overnight, and resuspended in 100 ml citrate buffer (0.1 M sodium citrate in 50% ethanol) to assess plating efficiency. Intensity of crystal violet staining, assessed at 570 nm and quantified using a Vmax Kinetic Microplate Reader and Softmax software (Molecular Devices Corp., Menlo Park, Calif.), was directly proportional to cell number. Data were normalized to vehicle-treated cells and are presented in FIG. 8 as the mean±SE from representative experiments. JS-014 and JS-020 were effective, and more potent than NPPTA, in inhibiting LCC9 (antiestrogen resistant) cells.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A method of treating breast cancer in a subject comprising administering to the subject one or more compounds of the following structure:

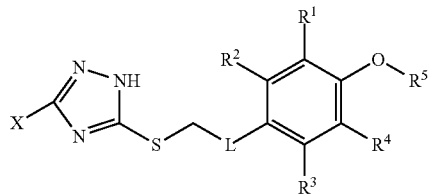

or a pharmaceutically acceptable salt or prodrug thereof, wherein:

L is —C(=O)NH—, —NHC(=O)—, —C(=O)O—, —C(=O)—CH₂—,

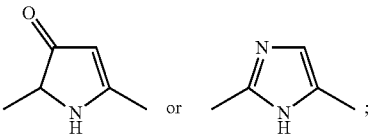

R¹, R², R³, and R⁴ are each independently selected from hydrogen, halogen, hydroxyl, trifluoromethyl, alkyl, heteroalkyl, amino, or alkoxyl;

R⁵ is substituted or unsubstituted aryl, cycloalkyl, alkynyl, or dansyl, wherein substituted aryl is substituted with alkyl, alkoxy, halogen, or haloalkyl; and X is aryl, heteroaryl, or cycloalkyl.

2. The method of claim 1, wherein R¹, R², R³, and R⁴ are each hydrogen, R⁵ is substituted or unsubstituted phenyl, L is —C(=O)NH—, and X is phenyl or pyridyl.

3. The method of claim 1, wherein R¹, R², R³, and R⁴ are each hydrogen, R⁵ is unsubstituted phenyl, L is —C(=O)NH—, and X is phenyl.

4. The method of claim 1, wherein R¹, R², R³, and R⁴ are each hydrogen, R⁵ is substituted phenyl, L is —C(=O)NH—, and X is pyridyl.

5. The method of claim 1, wherein R¹, R², R³, and R⁴ are each hydrogen.

6. The method of claim 1, wherein R⁵ is substituted or unsubstituted phenyl.

7. The method of claim 1, wherein L is —C(=O)NH—.

8. The method of claim 1, wherein X is aryl.

9. The method of claim 1, wherein X is phenyl.

10. The method of claim 1, wherein X is heteroaryl.

11. The method of claim 1, wherein X is pyridyl.

12. The method of claim 1, wherein the breast cancer is endocrine resistant breast cancer.

13. The method of claim 1, wherein the breast cancer is anti-estrogen resistant breast cancer.

14. A method of treating breast cancer in a subject comprising administering to the subject one or more compounds of the following structure:

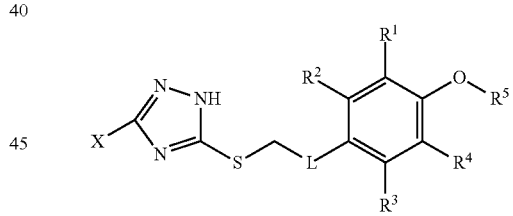

or a pharmaceutically acceptable salt or prodrug thereof, wherein:

L is —C(=O)NH—;

R¹, R², R³, and R⁴ are each hydrogen;

R⁵ is substituted or unsubstituted phenyl; and

X is phenyl or pyridyl.

15. The method of claim 14, wherein R⁵ is unsubstituted phenyl, and X is unsubstituted phenyl.

16. The method of claim 14, wherein R⁵ is substituted phenyl, and X is pyridyl.

* * * * *

UNITED STATES PATENT AND TRADEMARK OFFICE
CERTIFICATE OF CORRECTION

| | |
|---|---|
| PATENT NO. | : 10,806,725 B2 |
| APPLICATION NO. | : 15/155258 |
| DATED | : October 20, 2020 |
| INVENTOR(S) | : Dakshanamurthy et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 177 days.

Signed and Sealed this
Thirteenth Day of December, 2022

Katherine Kelly Vidal
*Director of the United States Patent and Trademark Office*